(12) United States Patent
Berzansky et al.

(10) Patent No.: US 8,589,181 B2
(45) Date of Patent: Nov. 19, 2013

(54) SYSTEMS AND METHODS FOR MANAGING MEDICAL INFORMATION

(75) Inventors: Kristi Innocenti Berzansky, South Park, PA (US); Binny John, Sterling Heights, MI (US); Kruti Goswami, Livonia, MI (US); Stanton McComb, Bloomfield Hills, MI (US); Shabari Madappa, Karnataka (IN)

(73) Assignee: McKesson Financial Holdings, Hamilton (BM)

( * ) Notice: Subject to any disclaimer, the term of this patent is extended or adjusted under 35 U.S.C. 154(b) by 0 days.

(21) Appl. No.: 13/434,309

(22) Filed: Mar. 29, 2012

(65) Prior Publication Data

US 2012/0185272 A1 Jul. 19, 2012

Related U.S. Application Data

(62) Division of application No. 12/167,744, filed on Jul. 3, 2008.

(60) Provisional application No. 60/948,383, filed on Jul. 6, 2007.

(51) Int. Cl.
*G06Q 50/00* (2012.01)
*G06Q 10/00* (2012.01)

(52) U.S. Cl.
USPC .................................................. 705/2; 705/3

(58) Field of Classification Search
USPC ........................................................... 705/2
See application file for complete search history.

(56) References Cited

U.S. PATENT DOCUMENTS

| | | | |
|---|---|---|---|
| 5,664,109 A | 9/1997 | Johnson et al. | |
| 5,737,539 A | 4/1998 | Edelson et al. | |
| 5,764,972 A | 6/1998 | Crouse et al. | |
| 5,771,657 A | 6/1998 | Lasher et al. | |
| 6,195,612 B1 * | 2/2001 | Pack-Harris | 702/2 |
| 6,464,142 B1 | 10/2002 | Denenberg et al. | |
| 6,493,427 B1 | 12/2002 | Kobylevsky et al. | |
| 6,668,188 B2 * | 12/2003 | Sun et al. | 600/513 |
| 6,942,146 B2 | 9/2005 | Pfutzenreuter et al. | |
| 7,069,278 B2 | 6/2006 | Telkowski et al. | |

(Continued)

OTHER PUBLICATIONS

Lundin, Moral hazard in physician prescription behavior, Sep. 2000, Journal of Health Economics, vol. 19, Issue 5, pp. 639-662, ISSN 0167-6296, http://dx.doi.org/10.1016/S0167-6296(00)00033-3.*

(Continued)

*Primary Examiner* — Tran Nguyen
(74) *Attorney, Agent, or Firm* — Alston & Bird LLP

(57) ABSTRACT

Systems and methods for managing medical information for medical service providers are provided. Personnel are able to manage and track workflow operations, evaluate profitability, and maintain records in an integrated and streamlined manner by executing various modules of a software application. A Dashboard module provides a unitary display of information regarding employee efficiency and operational profitability; a Virtual Will Call module allows for the virtual placement of items in storage areas reflecting the corresponding physical will call storage locations; an Rx Tracker module provides information regarding the status of prescriptions as they go through the process from ordered to dispensed; the Maintenance module allows personnel to define customized delivery methods; and the Archive Viewer module provides a way for personnel to archive images in any accessible drive or memory device, including portable storage media, and to view such images independently of the module using an archive viewer executable.

20 Claims, 31 Drawing Sheets

(56) References Cited

U.S. PATENT DOCUMENTS

| | | |
|---|---|---|
| 7,143,121 B2 | 11/2006 | Mendonca et al. |
| 2003/0097351 A1 | 5/2003 | Rothschild et al. |
| 2003/0146274 A1 | 8/2003 | Pfutzenreuter et al. |
| 2003/0149599 A1 | 8/2003 | Goodall et al. |
| 2003/0158469 A1 | 8/2003 | Elsayed et al. |
| 2004/0054685 A1* | 3/2004 | Rahn et al. ............ 707/102 |
| 2004/0122712 A1 | 6/2004 | Hill, Sr. et al. |
| 2004/0122713 A1 | 6/2004 | Hill, Sr. et al. |
| 2004/0122872 A1 | 6/2004 | Pandya et al. |
| 2005/0086074 A1* | 4/2005 | Punzak et al. ............ 705/2 |
| 2005/0216437 A1 | 9/2005 | Peairs et al. |
| 2005/0235140 A1 | 10/2005 | Hui et al. |
| 2006/0006222 A1 | 1/2006 | Brey et al. |
| 2006/0047720 A1 | 3/2006 | Kulkarni et al. |
| 2006/0149587 A1 | 7/2006 | Hill, Sr. et al. |
| 2006/0149796 A1 | 7/2006 | Aalmink |
| 2006/0167929 A1 | 7/2006 | Chakraborty et al. |
| 2006/0173708 A1 | 8/2006 | Vining et al. |
| 2006/0197979 A1 | 9/2006 | Kawasaki |
| 2006/0200508 A1 | 9/2006 | Telkowski et al. |
| 2006/0225383 A1 | 10/2006 | Cobb et al. |
| 2006/0235906 A1 | 10/2006 | Brinkmoeller et al. |
| 2007/0016648 A1 | 1/2007 | Higgins |
| 2007/0028110 A1 | 2/2007 | Brennan |
| 2007/0071294 A1 | 3/2007 | Mahesh |
| 2007/0079087 A1 | 4/2007 | Wang et al. |
| 2007/0124345 A1 | 5/2007 | Heinz et al. |
| 2007/0124346 A1 | 5/2007 | Mitchel et al. |
| 2007/0174364 A1 | 7/2007 | Wecker et al. |
| 2007/0192275 A1 | 8/2007 | Foygel et al. |
| 2007/0198630 A1 | 8/2007 | Jacobson et al. |
| 2007/0214369 A1 | 9/2007 | Roberts et al. |

OTHER PUBLICATIONS

Office Action for U.S. App. No. 13/434,107; dated Nov. 8, 2012.

Office Action for U.S. Appl. No. 13/433,914 dated Jan. 31, 2013.

United States Office Action for U.S. Appl. No. 13/433,914, dated Aug. 16, 2013.

* cited by examiner

| | E-PRESCRIBING | BATCH | | | | | | |
|---|---|---|---|---|---|---|---|---|
| RX ID | TYPE | STATUS | RECV DATE | LAST NAME | FIRST NAME | ITEM | PRESCRIBER | TIME RECIEVED |
| 572427 | REFILL | ERROR | MM/DD/YYYY | TIM | JACK | DRUG1 | PRESCRIBER1 | MM/DD/YYYY |
| 572447 | NEW RX | APPROVED | MM/DD/YYYY | JONES | TOM | DRUG2 | PRESCRIBER2 | MM/DD/YYYY |
| 572547 | REFILL | APPROVED | MM/DD/YYYY | HARRY | BLACK | DRUG3 | PRESCRIBER3 | MM/DD/YYYY |

| RX PROCESS HISTORY | | | |
|---|---|---|---|
| RX DETAILS | PROCESS HISTORY | | |
| DATE | ACTIVITY | USER | DESCRIPTION |
| | | | |
| | | | |
| | | | |
| | | | |

—184

CANCEL

FIG. 23

PREFERENCES

Tabs: GENERAL | DASHBOARD | IMAGING | FILLING | CHECKING | VIRTUAL WILL CALL | PHARMACY INFO
Sub-tabs: PREFERENCES | DELIVERY METHOD | REJECTION MESSAGE

DELIVERY METHODS

| | DELIVERY CODE | DELIVERY METHOD | TIME TYPE | TIME VALUE | DEFAULT | INACTIVE |
|---|---|---|---|---|---|---|
| | 0 | DELAY | NULL | NULL | | |
| | 1 | NORMAL | MIN | 00:30 | X | |
| | 2 | RUSH | MIN | 00:20 | | |
| | 3 | URGENT | MIN | 00:10 | | |
| △ | 4 | HOLD | NULL | NULL | | |
| | 5 | | | | | X |
| | 6 | | | | | X |
| | 7 | | | | | X |
| | 8 | | | | | X |
| | 9 | | | | | |

[APPLY]  [OK]  [CANCEL]

SYSTEMS AND METHODS FOR MANAGING MEDICAL INFORMATION

CROSS-REFERENCE TO RELATED APPLICATIONS

This application is a divisional of U.S. application Ser. No. 12/167,744 entitled "Systems and Methods for Managing Medical Information," filed Jul. 3, 2008, which claims priority to U.S. Provisional Application No. 60/948,383 entitled "Systems and Methods for Managing Medical Information," filed Jul. 6, 2007, the contents of each of which are incorporated herein in their entirety.

BACKGROUND

Service providers are always striving to maximize the efficiency of their day-to-day operations in order to provide accurate, reliable service to their customers, increase profitability, and ensure that all applicable laws and regulations are followed. This is especially true in the medical services industry, where mistakes can sometimes have injurious effects.

Pharmacies, for example, face several challenges when trying to streamline operations and provide quality service to their patients. Among other tasks, prescriptions must be filled and checked accurately to avoid dispensing the wrong medication; drug interactions and patient medical histories must be considered; prescriptions must be dispensed to the right patients as quickly as possible; and records must be kept (out of the way and, at the same time, easily accessible) for a period of time.

Coupled with the desire to provide quality service, medical service providers such as pharmacies must be profitable to maintain their daily operations. Several factors must be considered by managers and directors when evaluating profitability, such as employee efficiency, the cost of medications, and payments by insurance companies.

Thus, there exists a need for systems and methods of managing medical information for medical service providers to allow personnel to manage and track workflow operations, evaluate profitability, and maintain records in an integrated and streamlined manner.

BRIEF SUMMARY OF THE INVENTION

Systems and methods are therefore provided for managing medical information. Various modules are provided that, upon execution, allow users to more efficiently manage and track workflow operations, evaluate profitability, and maintain records.

In one exemplary embodiment, a method of managing activities for a medical service provider is provided. The method includes displaying a number of queues and a count of prescriptions in each queue and displaying productivity data including at least one user name and the prescriptions handled over a predetermined period of time by each user. The method further includes interfacing with at least one automated system and displaying a list of each interfacing automated system, as well as displaying profitability information including amounts paid for prescriptions and amounts approved for payment.

In some cases, a histogram is provided that includes a representation of at least one queue, such as a Pharmacy Management queue, an Imaging queue, a Filling queue, a Checking queue, and/or a Will Call queue. Different subsections of each queue within each representation may be depicted differently. Also, an indication of at least one event associated with at least one of the queues may be provided, and a selection of the indication may be permitted such that the selection provides for a display of additional information regarding the respective indication.

In some embodiments, a log in status of each user and a list of log in and log out times may be provided upon selection of a respective user. Furthermore, the productivity data may be provided in a graphical representation and/or in a tabular representation. Interfacing with the automated system(s) may include providing at least one characteristic of each interfaced automated system, such as a number of cells that need replenishment and/or a number of cells that need cleaning. Also, the designation of a time period over which the profitability information is calculated and displayed may be received. A graphical representation of at least one workflow characteristic, such as a prescription volume and/or an average cycle time for processing prescriptions, may be displayed.

In another exemplary embodiment, a method of tracking the inventory of medical supplies for a medical service provider is provided. The method includes receiving a prescription identifier for a prescription to be stored or removed from will call, receiving a designation of a location in which the prescription will be stored, and displaying a visual representation of the location amongst a number of locations in a respective storage area. The prescription identifier may be, for example, a scanned barcode or a keyed user input.

In some cases, input may be received, and at least one aspect of the visual representation, such as the configuration of the storage area and/or the designation of the location, may be changed based on the input. Input may also be received regarding the transfer of the prescription from the location to a different location, and the visual representation may be modified accordingly. Receiving the prescription identifier may include validating a prescription number associated with the prescription. The number of prescriptions stored in the location may also be displayed in some embodiments. Furthermore, a location for storage of the prescription may be suggested based on information associated with the prescription identifier.

In another exemplary embodiment, a method of maintaining and updating records for a medical services provider is provided. The method includes receiving at least one search criterion regarding a prescription, displaying information associated with the search criterion received, and presenting an indication of whether proactive counseling of a patient associated with the prescription is required upon the patient's subsequent visit. Presenting the indication may include displaying a flag, notes, or other indicator regarding the proactive counseling required. Furthermore, input may be received indicating that the proactive counseling has been accomplished, and the indication may be modified based on the input.

At least one item of information, such as prescription details, process history of the prescription, patient details, profitability information, or images associated with the prescription may be presented. Also, input regarding the prescription may be received, and the information associated with the prescription may be modified based on the input.

In another exemplary embodiment, a method of customizing the delivery of medical supplies for a medical services provider is provided. The method includes receiving a designation of a delivery method for a prescription, associating the delivery method to a delivery time of the prescription, and prioritizing a list of prescriptions according to the delivery method and associated delivery time.

In some cases, the prioritized list of prescriptions may be displayed. Furthermore, input regarding the delivery method may be received, and the delivery method may be modified according to the input received. The uniqueness of the modified delivery method as compared to existing delivery methods may also be verified.

In another exemplary embodiment, a method of archiving images for a medical services provider is provided. The method includes receiving a selection of at least one image to be archived via an archiving application, receiving a designation of a source of the at least one image, and receiving a designation of a location in which the at least one image is to be archived. The method further includes storing the image(s) in the location and creating an archive viewer executable at the location such that the image(s) may be viewed from the location independently of the archiving application.

In some embodiments, the image(s) may be deleted from the source. Also, information may be displayed regarding past archiving activities. Such information may include at least one item such as a start date and an end date of archived data, the respective source, the respective location, a date of an archive activity, a designation of a user who performed the archive activity, and/or a password associated with the archived data, among others. In some cases, the designation of the source may be a designation of a prescription database or a patient database.

An archive log may also be created at the designated source to record an archive activity. In addition, a start date for data to be archived may be pre-selected based on an end date of the last archive activity performed. Furthermore, the method may include determining whether the space at the location is adequate for storing the image(s) and prompting a designation of an alternate location if the space is inadequate.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 4 shows an example of a Pharmacy Management queue of a Dashboard module according to an exemplary embodiment of the present invention;

FIG. 17 shows an example of a Maintain tab of a Virtual Will Call module according to an exemplary embodiment of the present invention;

FIG. 18 shows an example of an Rx Tracker screen of an Rx Tracker module according to an exemplary embodiment of the present invention;

FIG. 21 shows an example of a View Rx screen of an Rx Tracker module according to an exemplary embodiment of the present invention;

FIG. 23 shows an example of a Process History screen of an Rx Tracker module according to an exemplary embodiment of the present invention;

FIG. 24 shows an example of a Delivery Method tab of a Maintenance module according to an exemplary embodiment of the present invention;

FIG. 28 shows an example of a Search screen of an Archive Viewer module according to an exemplary embodiment of the present invention;

FIG. 30 shows an example of a Packing Box configuration screen according to an exemplary embodiment of the present invention.

DETAILED DESCRIPTION

Figure 1A:
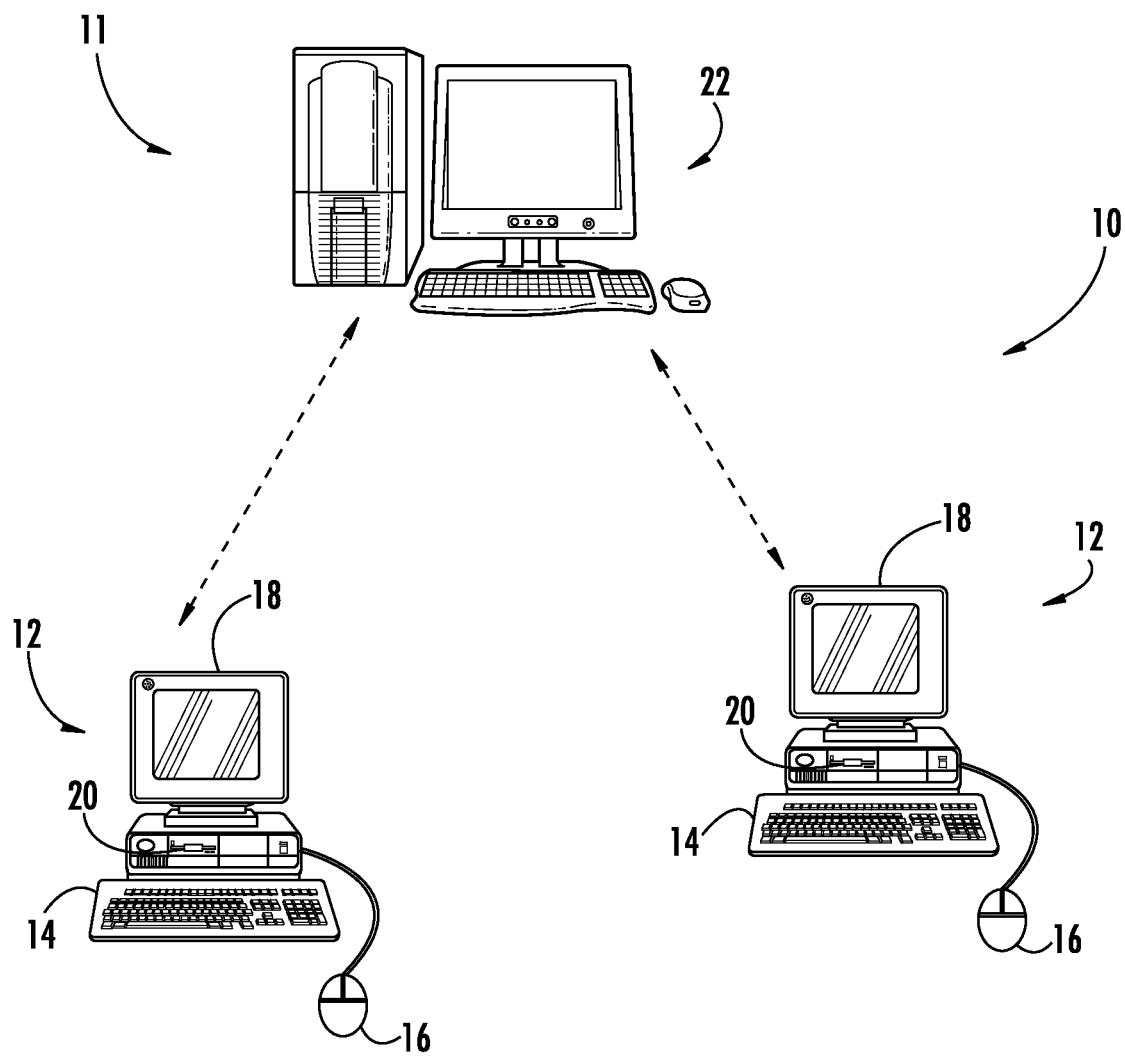
FIG. 1A illustrates a typical environment in accordance with one exemplary embodiment of the present invention.

Embodiments of the present inventions now will be described more fully hereinafter with reference to the accompanying drawings, in which some, but not all embodiments of the inventions are shown. Indeed, embodiments of these inventions may be embodied in many different forms and should not be construed as limited to the embodiments set forth herein; rather, these embodiments are provided so that this disclosure will satisfy applicable legal requirements. Like reference numerals refer to like elements throughout.

The systems and methods of the present invention may be used by medical service providers, such as hospitals, physicians' offices, pharmacies, and any other distributor of medical supplies, to facilitate day-to-day operations and workflow management. The systems and methods described provide an integrated platform for monitoring and managing inventory, tracking staff activities, storing records and images, and aiding communication between medical professionals and their patients. The systems and methods may be stand-alone applications, or they may communicate with other automated systems being implemented by the medical service provider to provide a user with an integrated solution for managing the distribution of medical supplies and caring for patients, as will be described below.

FIG. 1A illustrates an example of a typical environment 10 in which the systems and methods of embodiments of the present invention may operate. For the purposes of explanation, the environment 10 will be described in terms of a pharmacy setting, although it is understood that the systems and methods of embodiments of the present invention may be used in any setting where medical supplies are handled, supplied, and/or distributed. A system 11 typically includes one or more workstations 12, where pharmacists, technicians, and other personnel can access information regarding patients, prescriptions, and pharmacy operations according to embodiments of the present invention. In this regard, each workstation 12 may include one or more user input devices, such as a keyboard 14, a mouse 16, or other input device for entering data. Each workstation 12 may also include a display 18 for displaying information to a user, as well as one or more input data ports 20 for importing data from or exporting data to an external data storage medium, such as a Compact Disc (CD), floppy disk, Universal Serial Bus (USB) device, or the like.

The system 11 may also include a server 22 or other computing device in communication with each workstation 12. The server 22 may be used to store data that may be accessed by each workstation 12 as necessary. The server 22 may be co-located with the workstations 12, for example in the same pharmacy, or the server 22 may be located elsewhere, such as outside the pharmacy in the same building or in another building. For example, in some cases the server 22 may include a database storing patient records for a hospital and may be located in the basement of the hospital in which the pharmacy is located. As another example, the server 22 may hold data regarding the medical supply inventory for several pharmacies distributed throughout a certain geographic region. The server 22 and workstations 12 may communicate and exchange data via a wired or wireless connection. For example, the server 22 and workstations 12 may be connected via a Wide Area Network (WAN) and exchange data via the Internet. For instance, the server 22 and the workstations 12 may be connected to a common pharmacy network.

Figure 1B:
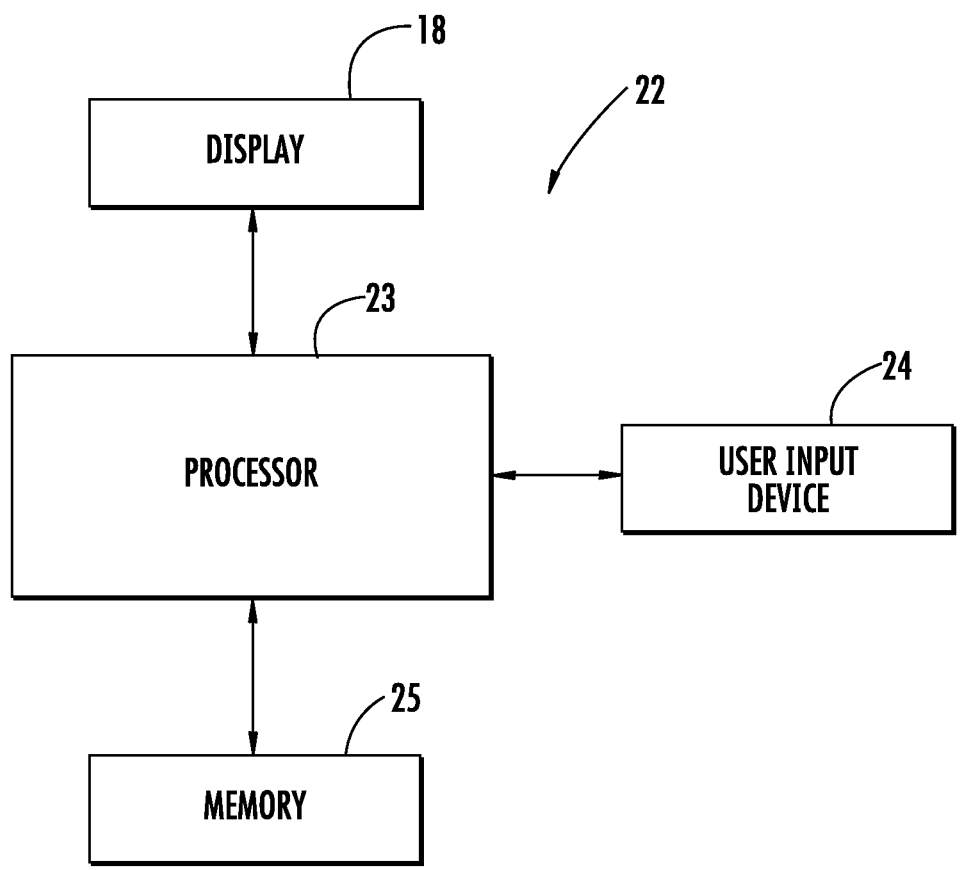
FIG. 1B is a schematic representation of a computing device in accordance with one exemplary embodiment of the present invention.

While embodiments of the present invention may be deployed in a client-server architecture, it may be deployed in other architectures as well. FIG. 1B depicts a hardware block diagram of the server 22 or other computing device having a processor 23, a user input device 24 (keypad, touchscreen, bar code scanner, etc.), a display 18 and memory 25. Memory 25 may be used to store computer program instructions, such as software, that are accessible and executable by the processor 23 to perform the various functions described herein. For example, the software may include each of the modules described below. It should be noted, however, that while the various aspects of the invention are described as modules, one or more of the functions may be integrated and need not be modularized. Memory 25 may also be used to store information input via the various modules, such as archived data, will call location information, information to allow the tracking of a prescription, etc. While a single block representing memory is shown, the memory 25 can be distributed and may include many different types of memory.

Referring again to FIG. 1A and considering the example of the pharmacy setting, pharmacists, technicians, and other authorized personnel may use one of the workstations 12 to access a software application according to the systems and methods of the present invention in order to perform various functions related to inputting, filling, tracking, checking and imaging prescriptions. A user, such as a pharmacist, may log on to one of the workstations 12 and access the software application by inputting a user name and providing an authorization identifier, such as a password, fingerprint, or other biometric identifier, to establish that the user is authorized to access the application. Once the user has successfully accessed the application, the user will have the option of choosing a module of the application to perform a certain function, as described below.

Figure 2:
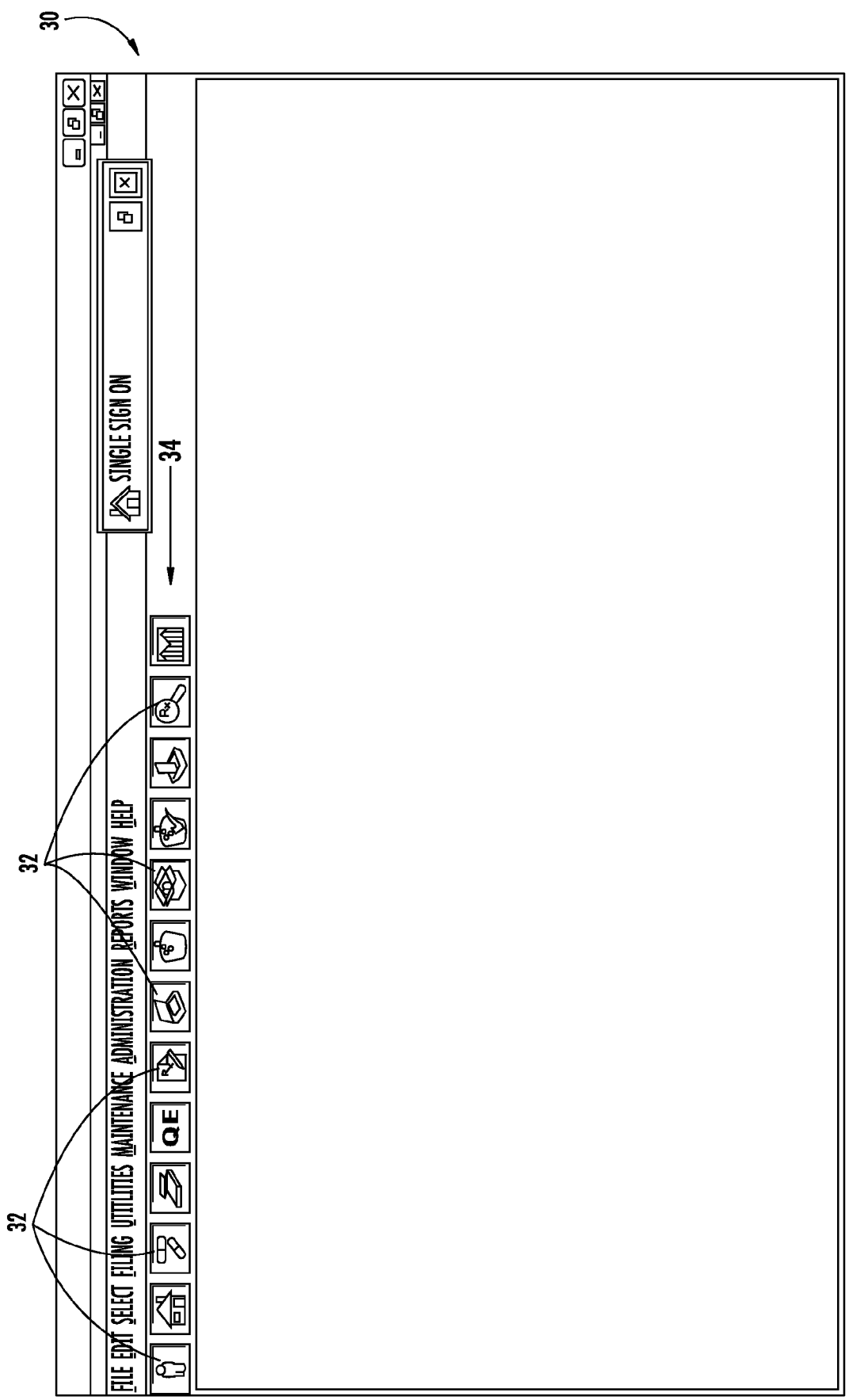
FIG. 2 shows an example of a user interface with a toolbar containing icons for modules according to an exemplary embodiment of the present invention.

FIG. 2 illustrates a user interface 30 provided by one embodiment of the systems and methods of the present invention. The user interface 30 may be provided once a user has gained access to the software application and may present the user with the option of accessing one of several modules 32, which may be presented in the form of tabs or a toolbar 34, as shown. Each module 32 may provide the user with the ability to perform certain functions, such as viewing patient information, tracking a prescription, and archiving images, to name a few. Each module 32 may be accessible only to users with certain permissions. For example, although any member of the pharmacy staff may be authorized to track a prescription using one module, only licensed pharmacists may be authorized to view patient details using another module, and only the director of the pharmacy may be authorized to view profitability information using yet another module. Several of the modules that may be included in the application are described below with reference to the figures.

Dashboard Module

Figure 3:
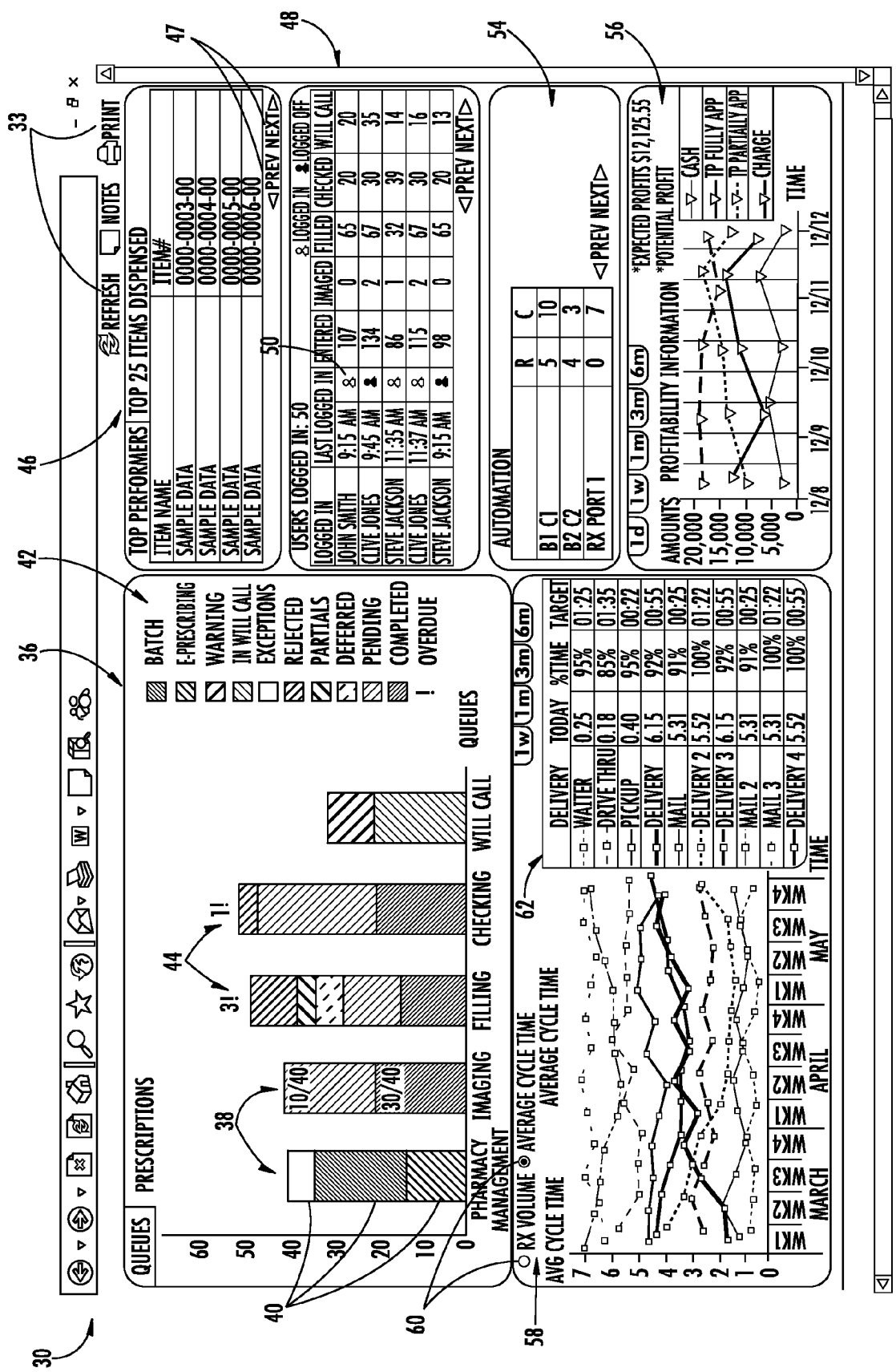
FIG. 3 shows an example of a Dashboard module according to an exemplary embodiment of the present invention.

One of the modules that may be selected by a user with appropriate permissions is the Dashboard module. A user interface 30 that may be displayed upon execution of the Dashboard module is illustrated in FIG. 3. The Dashboard module may be used by individuals including pharmacists, clerks, dispensing technicians, and managers, to view key metrics relating to the operations of the pharmacy in graphical and textual form. Information provided in any portion of the Dashboard module may be refreshed or printed by the user, for example by clicking on a respective icon or button 33 using the user input device. It should be noted that reference to "clicking" on an item/function/icon/etc. includes selecting the item/function/icon/etc. and is not limited to the act of clicking. Rather, "clicking" includes selection done by text entry, selection from a drop down or other menu or the like.

The interface 30 may include various windows displaying different information. For example, the interface 30 of FIG. 3 includes a Queues window 36 showing a histogram that describes the number of prescriptions in each queue, such as a Pharmacy Management queue, Imaging queue, Filling queue, Checking queue, and Will Call queue. Thus a user may see how many prescriptions are waiting in a particular step of the process of dispensing the medication to a patient.

Each bar 38 of the histogram, representing a queue, may be further divided into subsections 40 for displaying different values within each queue. For example, under the Pharmacy Management queue, the number of prescriptions in E-prescribing, Batch queue (prescriptions in the re-fill batch queue), and Workflow Exceptions (e.g., prescriptions that have been rejected at filling, rejected at checking, or returned or removed from Will Call) may be displayed using different colors as indicated by a legend 42 on the histogram. The Imaging queue may display the number of prescriptions that completed imaging during that day and the number of prescriptions pending to be imaged, as will be described below. The Filling queue may display the number of prescriptions that completed filling during that day and the number of prescriptions pending to be filled, as well as the number of prescriptions in the filling deferred and partial queues and those rejected in filling. The Checking queue may include the number of prescriptions that completed checking during that day and the number of prescriptions pending to be checked or rejected in checking. Similarly, the Will Call queue may display the number of prescriptions that are currently placed in Will Call and those that meet the requirements for maximum retention days or warning days.

Further indications may be included for at least some of the queues to make the user aware of certain events. For example, for the Filling and Checking queues in FIG. 3, an overdue flag 44 (shown as an exclamation point in FIG. 3) may be included to denote the number of prescriptions that are currently overdue in the respective queue. A user's selection of the overdue flag may serve to launch another module, such as the Rx Tracker (described below), in order to display details regarding the particular overdue prescriptions in the queue.

A user may also see more details in the Queues window 36 by using an input device, such as a mouse, to hover over or click on a particular bar 38 or bar subsection 40. For example, hovering over or clicking on a subsection 40 may cause the number of prescriptions in the category represented by the subsection to be displayed. Hovering or clicking may also cause another screen 45 to be displayed showing further details regarding a particular queue, such as the Pharmacy Management queue as illustrated in FIG. 4.

Referring again to FIG. 3, a Performers window 46 may be included to display to the user the top items dispensed overall, such as the top 25 items. For example, the name of the medication and item number may be presented in grid format starting with the most dispensed item. If fewer than the total number of items are displayed in the Performers window 46 due to space constraints, a scroll bar or buttons 47 may be provided to allow a user to view subsequent or previous top performers. Alternatively or in addition to scrolling, the complete list of items may be displayed when the user hovers over or clicks on the partial list. Items included on the list may vary depending on the configuration of the metric. For example, the time period for calculating the number of items dispensed, as well as the types of prescriptions that are excluded from the count (such as prescriptions that are on hold, canceled, etc.), may be configured by a user with authorization to provide a useful metric.

Figure 5:
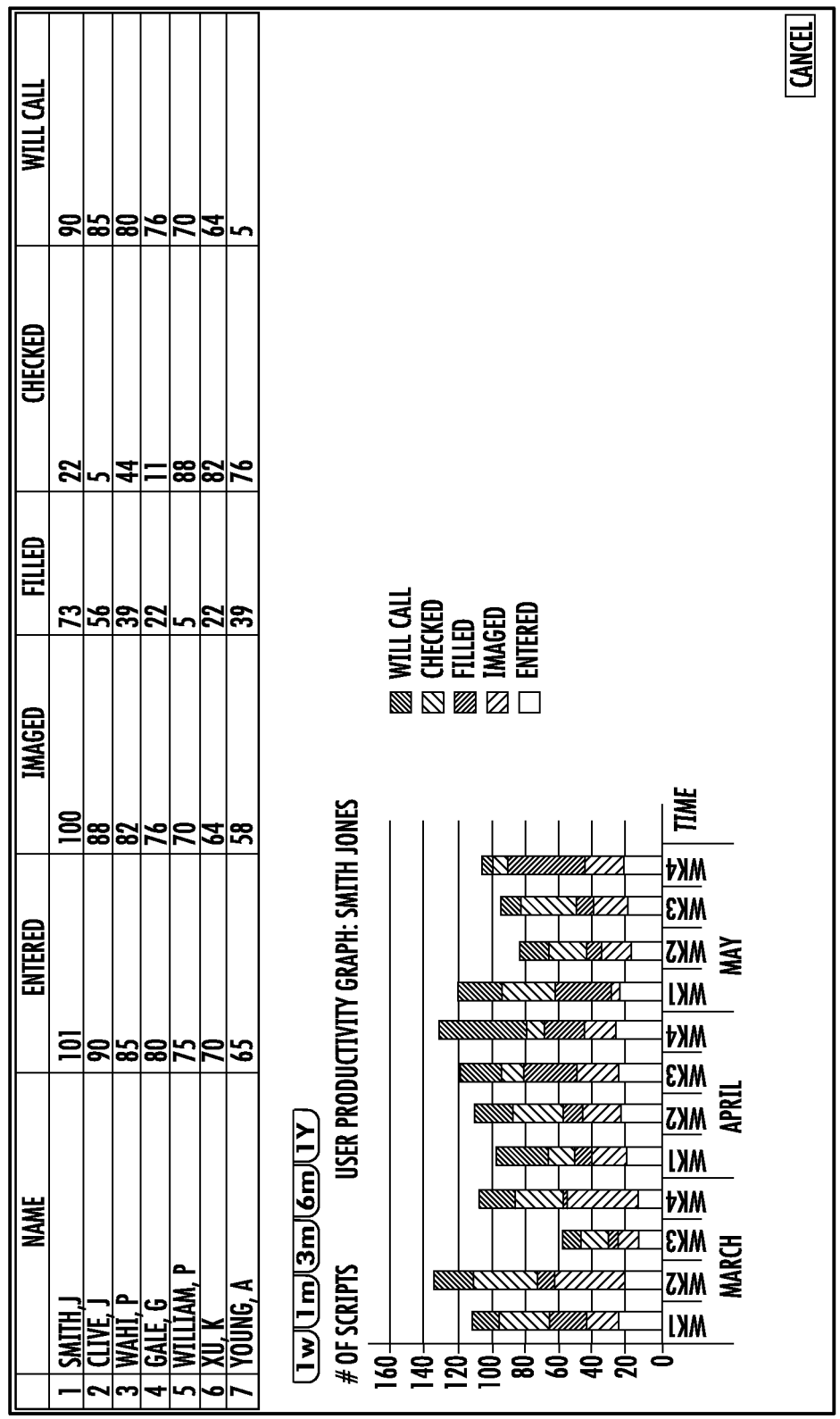
FIG. 5 shows an example of a screen containing User Productivity information of a Dashboard module according to an exemplary embodiment of the present invention.

A User Productivity window 48 may also be included to present information regarding users that are logged into the system. Information such as the user's name, last log in time, status (i.e., currently logged in or not currently logged in), the number of prescriptions entered, imaged, filed, and/or checked by the user, and the number of prescriptions stored in Will Call by the user may be displayed in tabular form. The status of the user may be indicated using text or via an icon 50, as shown in FIG. 3. Additional information, such as a list of log in and log out times for each user for the day, may be provided upon selection of a user (e.g., clicking on the user's name or elsewhere in a given entry for a user). Furthermore, clicking anywhere in the User Productivity window 48 may cause another screen 52 to be displayed showing user productivity information in tabular and graphical form, as shown in FIG. 5. The columns of the table may be sortable by the user.

Referring again to FIG. 3, an Automation Details window 54 may be provided that lists automation units in the pharmacy that are available for interfacing with the system 11. Automation units may include devices that use counting technology to count pills and the like, such as Baker Cells® and Baker Cassettes® devices. For example, in FIG. 3, three automation units are available: Unit 1, Unit 2, and Rx Port 1. In addition to the name of each unit, the number of cells that need replenishment (R) and the number of cells that need cleaning (C) may also be listed. If a particular unit has no cells in need of replenishment or cleaning, however, that unit may not be displayed. Upon clicking on the replenishment count (or cleaning count) for a particular unit, a screen may be displayed providing further details, such as the Bank, Cabinet, Cell, and Replenishment Status (or Cleaning Status, respectively) of the selected unit.

A Profitability window 56 may also be included in the interface 30 and may display information relating to the profitability of pharmacy operations. For example, the approved dollar amount received for a period of time may be included in the profitability calculations, cash received, amounts fully approved for payment, and/or amounts partially approved for payment, and others as configured by an authorized user, such as the pharmacy director. Profitability information may be calculated and displayed, based on user preferences, for various time periods, such as 1 day, 1 week, 1 month, 3 months, 6 months, etc. and may be presented in graphical form, as shown.

Figure 6:
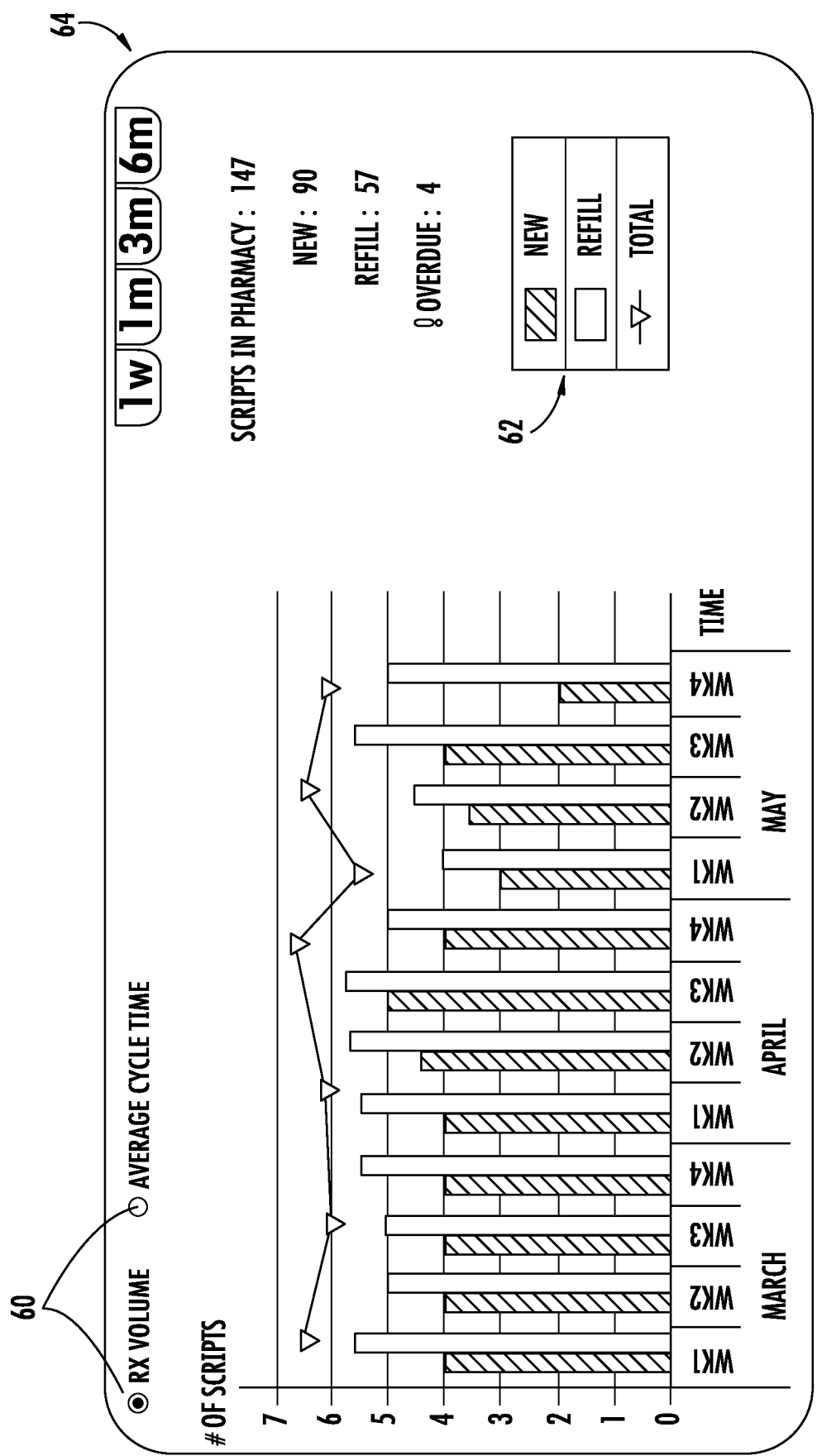
FIG. 6 shows an example of Prescription Volume information of a Dashboard module according to an exemplary embodiment of the present invention.

Furthermore, an Average Cycle Time/Prescription Volume window 58 may be provided and may include information regarding the average cycle time of prescriptions and prescription volumes. For example radio buttons 60 may be provided to allow a user to select which set of data (cycle time or volume) to present in graphical form. In FIG. 3, the radio button for displaying information on Average Cycle Time is selected, and the corresponding graph is displayed. Average Cycle Time data may include the time required to process a prescription in the pharmacy for each delivery method. The data may be presented for various time frames, as previously discussed. A legend 62 may also be provided to supply additional information regarding the selected graph. Prescription Volume information may include the number of total, new, and refill prescriptions received in the pharmacy, as well as an indication of any overdue prescriptions. An example of Prescription Volume information 64 is illustrated in FIG. 6. Details regarding the data presented in graphical form (Average Cycle Time data or Prescription Volume data) may be provided upon a user's hovering over or selecting a particular data point on the graph.

Virtual Will Call Module

Another module that may be included in the software application according to embodiments of the systems and methods of the present application is a Virtual Will Call module. A pharmacy may have several locations for storing medication that has been prepared for a patient according to a prescription and is waiting to be picked up by that patient. Depending on the type of medication, the item may need to be maintained in a refrigerator, in a narcotic vault, or may be too bulky to be kept with other will call prescriptions. As such, some medications may get "lost" in an obscure or infrequently visited will call location if the location is not properly tracked.

The Virtual Will Call module provides a way for users to keep track of the will call location of each filled prescription. In general, the Virtual Will Call module allows a user to set up custom "locations" that mirror physical locations in the pharmacy where items may be stored to await pick-up. In this way, each filled prescription may be associated with a location in Virtual Will Call corresponding to its physical location in the pharmacy.

Figure 7:
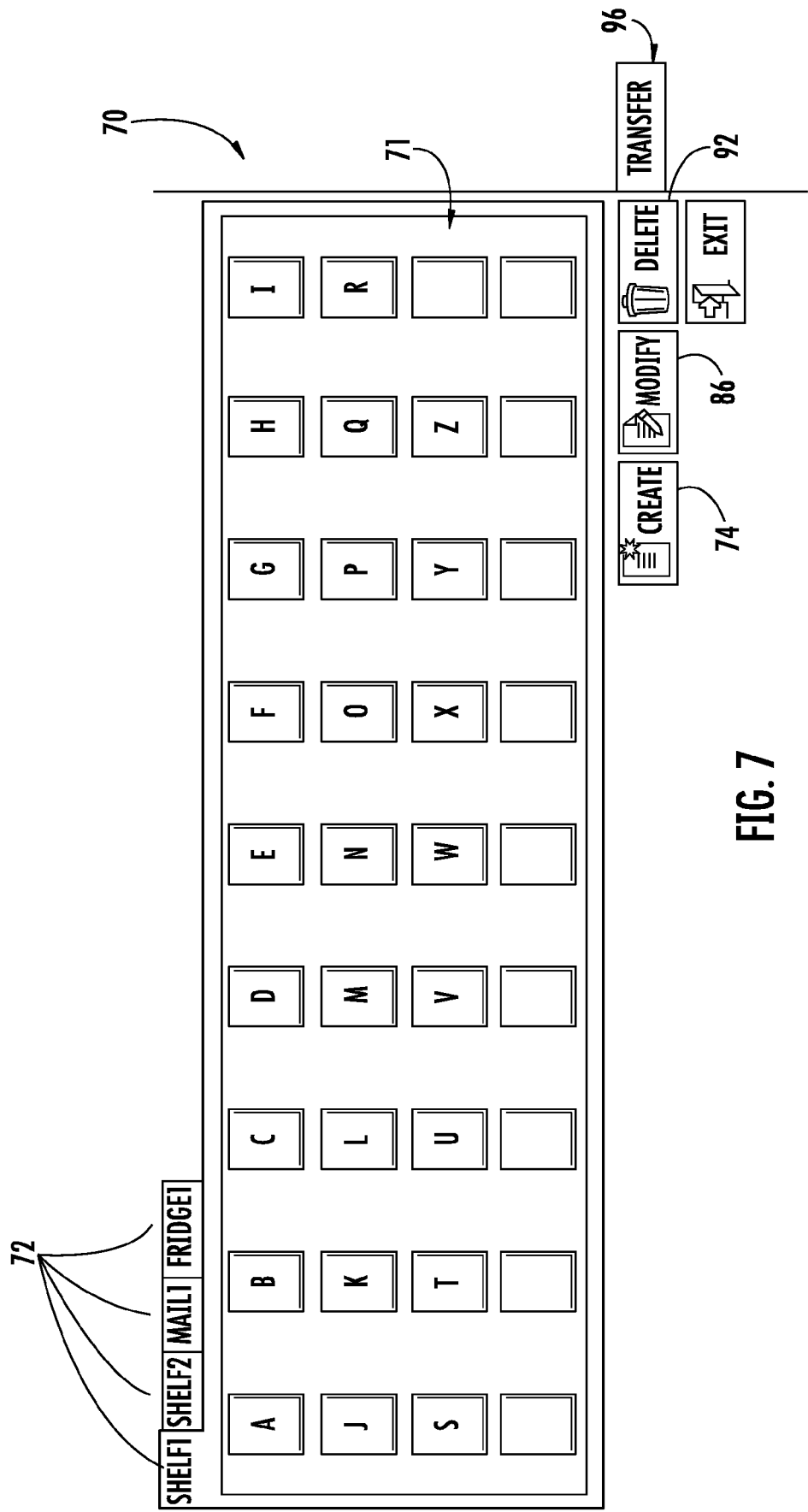
FIG. 7 shows an example of a Set Up screen of a Virtual Will Call module according to an exemplary embodiment of the present invention.

A Virtual Will Call area may be set up by any user with permission on the system to do so. Such a user may be presented with a Set Up screen 70, shown in FIG. 7, to allow the user to configure the virtual will call area. Storage Area tabs 72 may be provided corresponding to any will call areas that are already set up. For example, FIG. 7 shows that one or more users have already set up four Storage Areas: Shelf 1, Shelf 2, Mail 1, and Fridge 1. A diagram 71 of the layout of each Storage Area may be displayed under each tab 72.

Figure 8:
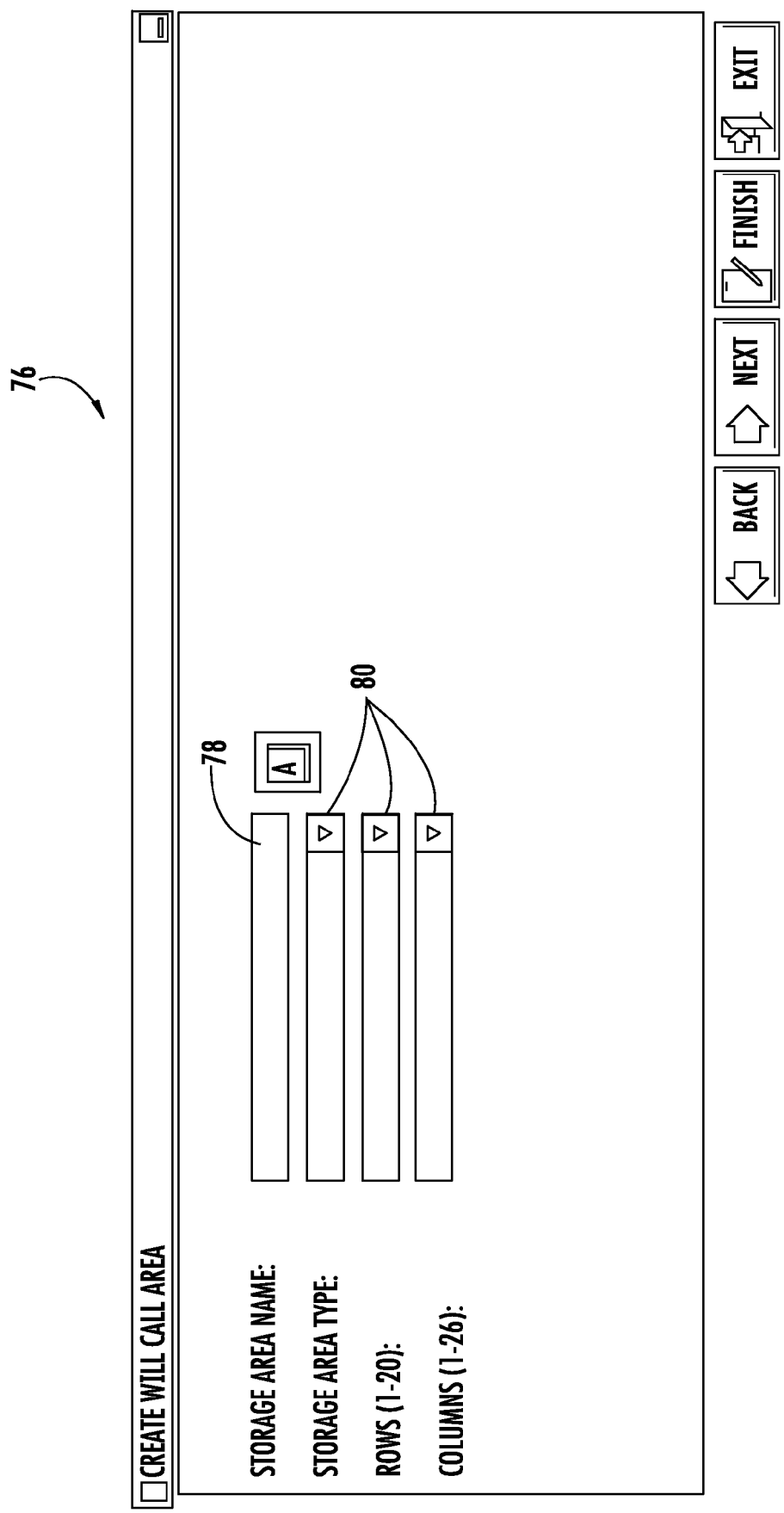
FIG. 8 shows an example of a Create screen according to an exemplary embodiment of the present invention.

If the required Storage Area does not already exist, the user may choose the "Create" option by clicking on the Create button 74. Upon doing so, a Create screen 76 may be displayed that may provide a text field 78 for the user to input a Storage Area Name, illustrated in FIG. 8. Drop down menus 80 may also be provided to allow a user to select a Storage Area Type (such as Shelf, Refrigerator, Delivery, Mail, Compounding, Bulk, Long Term Care, Narcotic Vault, etc.) and define the number of rows and columns to be associated with the particular will call location.

Figure 9:
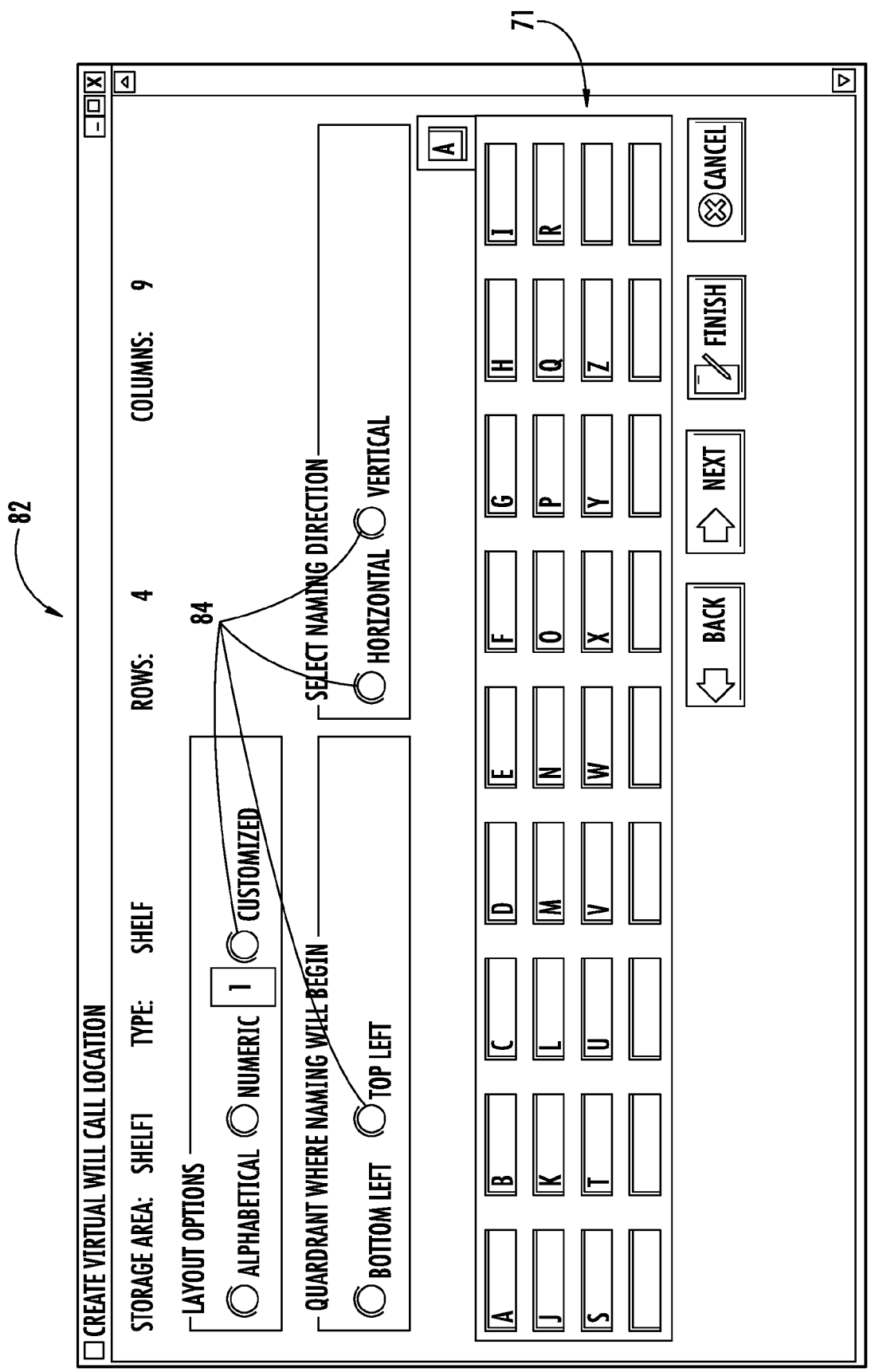
FIG. 9 shows an example of another Set Up screen of a Virtual Will Call module according to an exemplary embodiment of the present invention.

If the Storage Area Name is unique and the information provided is acceptable by the system, a third Set Up screen 82 may be displayed to provide further options for configuring the will call location, shown in FIG. 9. For example, the layout of the Storage Area may be configured by the user to be alphabetical (cells named A, B, C, etc.), numeric (cells named numerically starting from a value specified by the user), or customized (cells named according to user inputted names), and the starting point and naming direction may be defined using radio buttons 84. A diagram 71 showing the resulting configuration may be displayed to allow the user to visually verify the layout of the will call location and change the cell names as desired.

Figure 10:
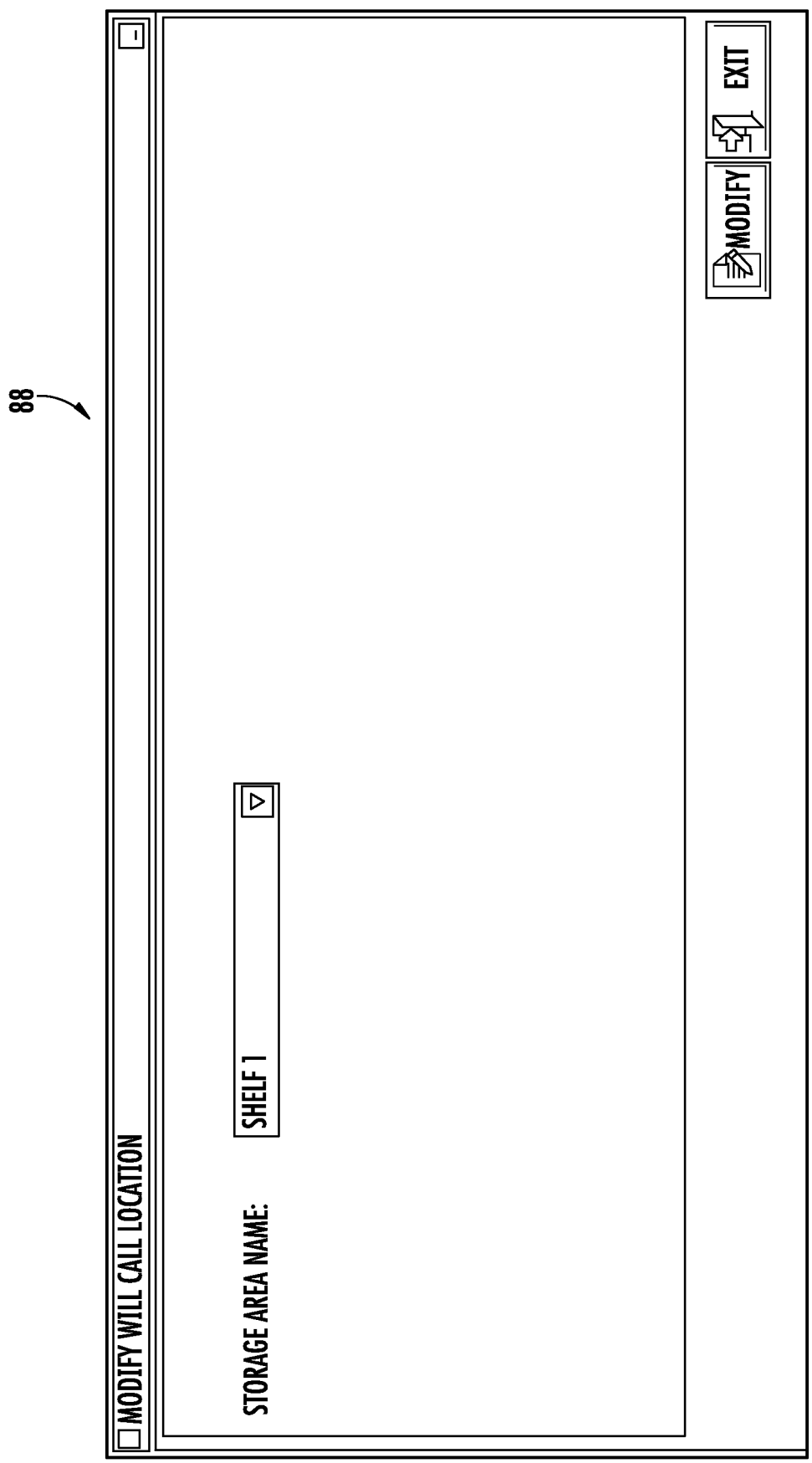
FIG. 10 shows an example of a Modify screen of a Virtual Will Call module according to an exemplary embodiment of the present invention.
Figure 11:
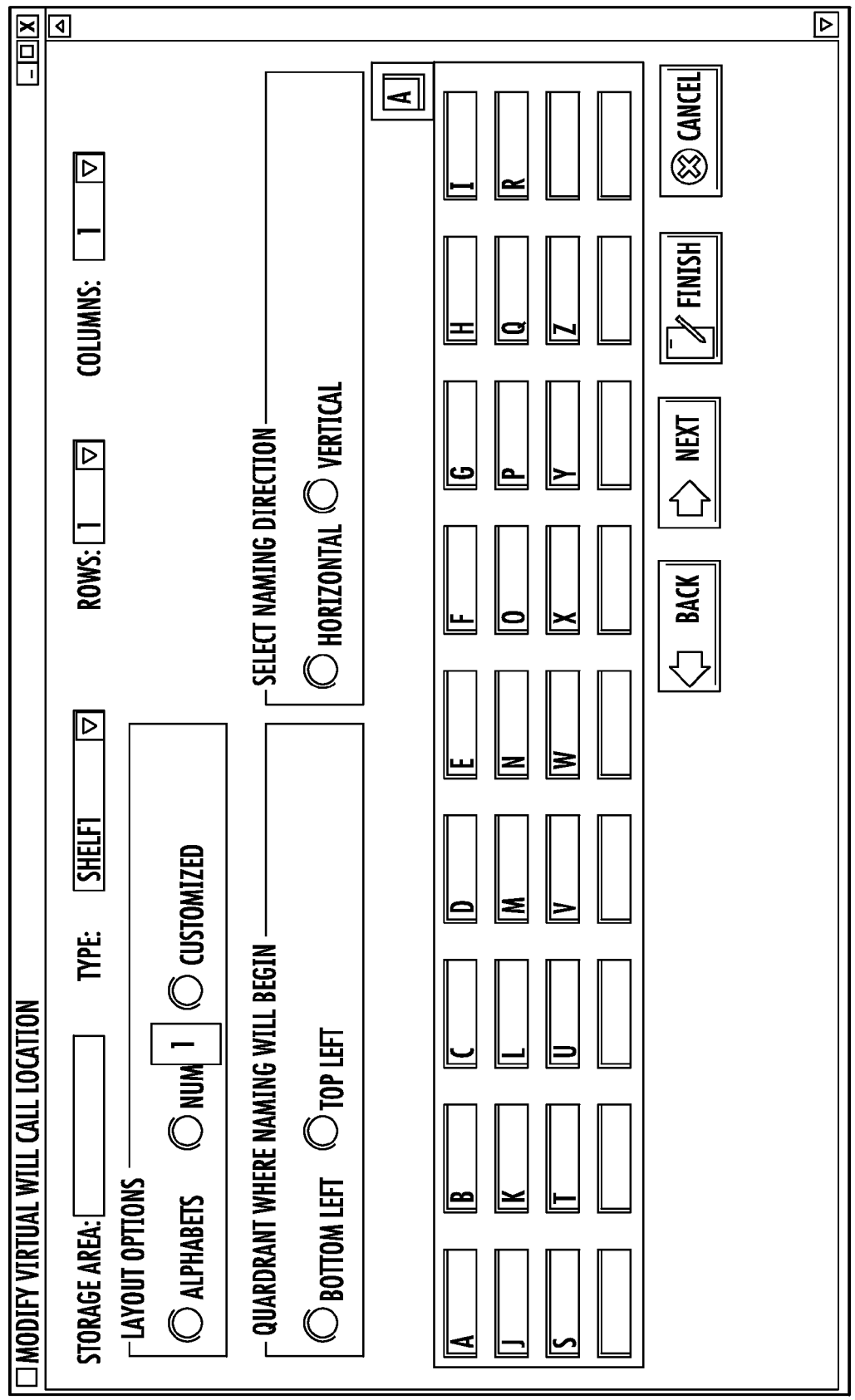
FIG. 11 shows an example of another Modify screen of a Virtual Will Call module according to an exemplary embodiment of the present invention.
Figure 12:
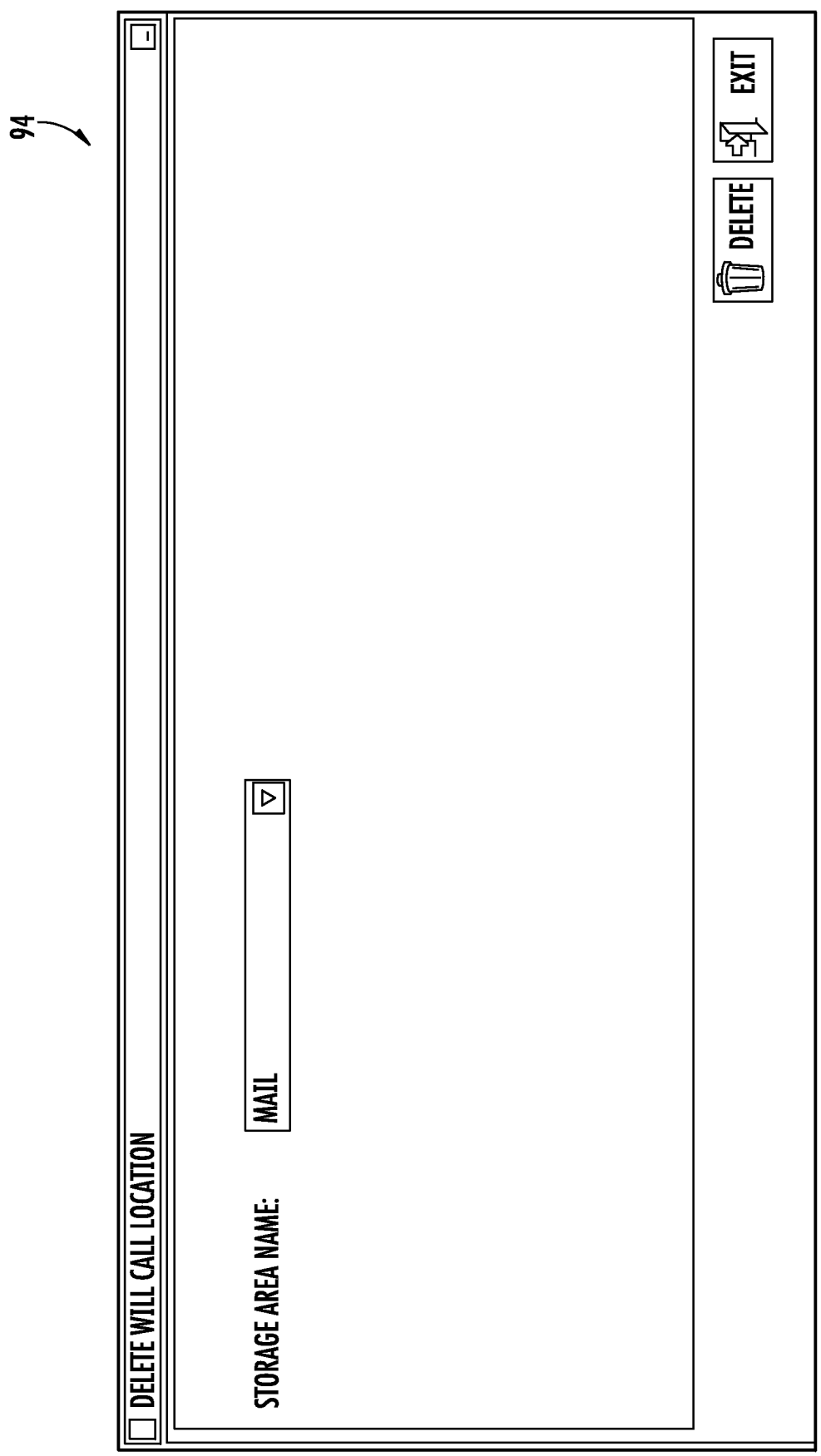
FIG. 12 shows an example of a Delete screen of a Virtual Will Call module according to an exemplary embodiment of the present invention.
Figure 13:
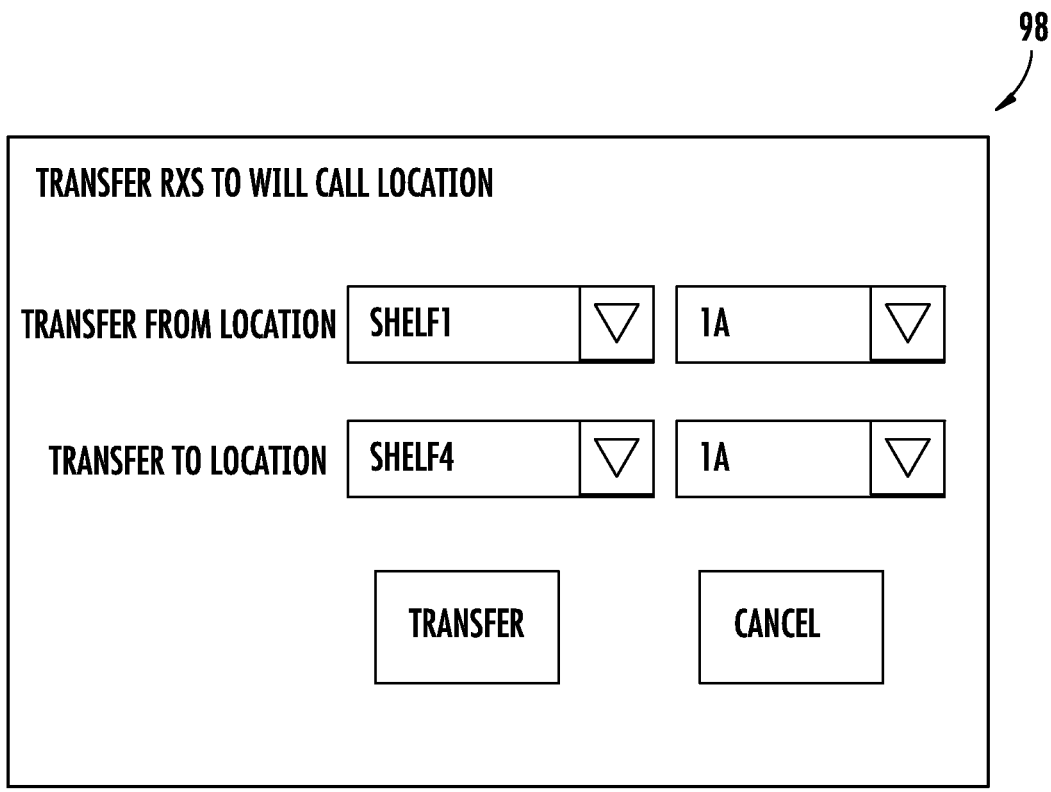
FIG. 13 shows an example of a Transfer screen of a Virtual Will Call module according to an exemplary embodiment of the present invention.

Existing Storage Areas may also be modified by a user by selecting the Modify button 86, shown in FIG. 7. Upon selection of this option, a Modify screen 88 may be displayed (shown in FIG. 10) allowing the user to select a Storage Area to modify. A second Modify screen 90 (shown in FIG. 11) may then be displayed, including editable fields for the user to perform modifications on the selected will call location. The user may be able to modify the area name, and/or the number of rows and columns; however, the user may not be allowed to reduce the number of rows or columns if prescriptions are already associated with the rows or columns to be deleted. In this case, the user may have to move the prescriptions to a different cell, as described below, before performing the desired modifications. Similarly, storage areas may be deleted using the Delete button 92 (FIG. 7), which in turn displays a Delete screen 94 (FIG. 12). Again, prescriptions may have to be moved to a different location before a delete operation is allowed, if the prescription is associated with a cell to be deleted. From the screen shown in FIG. 7, the user may change the location of a prescription by selecting the Transfer button 96. A Transfer screen 98 may then be displayed, as shown in FIG. 13, allowing the user to specify the location to which a given prescription is to be transferred.

Once a Storage Area has been set up and configured according to the user's preferences, prescriptions may be stored in the appropriate Storage Area (i.e., associated with virtual will call locations corresponding to their physical locations in the pharmacy). A user may store a prescription in a Storage Area if, for example, the prescription has a status of Checked (e.g., the pharmacist has checked that the prescription was filled properly), In Will Call (the prescription has been placed in Will Call), Will Call Removed (the prescription has been removed from Will Call), Filled (the prescription has been counted by the filling technician and is ready to be checked), or Ready for Filling (the prescription is in the Filling queue waiting to be checked). The user may select the Virtual Will Call module from the toolbar 34 (FIG. 2) or may have the option of storing the prescription while executing functions in other modules, such as Checking. User inputs regarding the virtual will call location and associated information regarding the patient and prescription may be stored in memory for subsequent recall and/or searching, as previously discussed.

Figure 14:
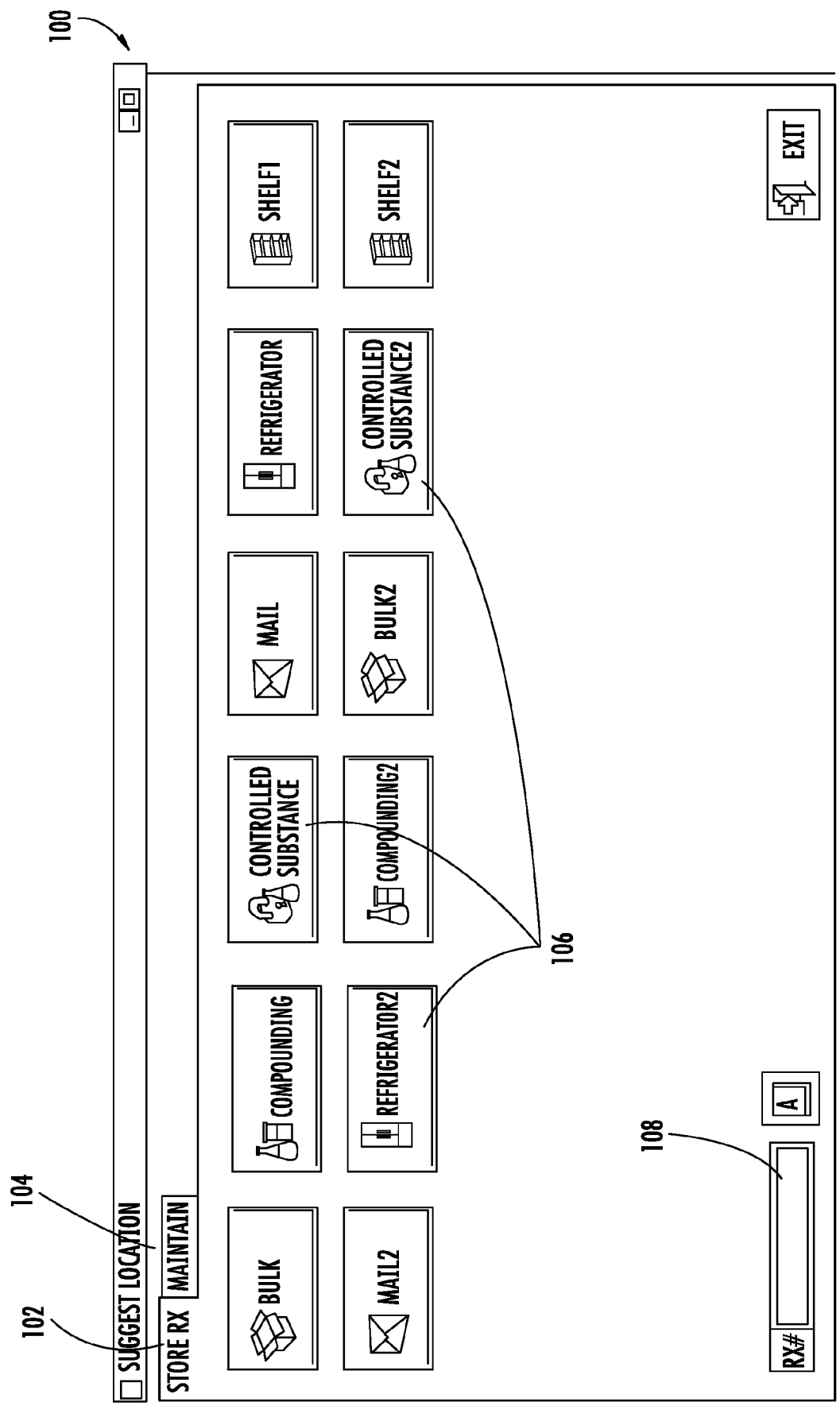
FIG. 14 shows an example of a Store screen of a Virtual Will Call module according to an exemplary embodiment of the present invention.

Once Virtual Will Call is initiated, a Store screen 100 may be displayed, such as the screen shown in FIG. 14. The Store screen 100 may include multiple tabs, such as a Store Rx tab 102 and a Maintain tab 104, described below. Under the Store Rx tab 102, various buttons 106 representing each available Storage Area of will call may be displayed. The user may then be able to enter the prescription number manually, such as by typing the number in a text field 108, or may be able to input the prescription number by scanning in a bar code of the prescription. If the prescription is scanned, the system may then decode the scan to obtain the prescription number. The system may then confirm that the prescription number is valid.

Figure 15:
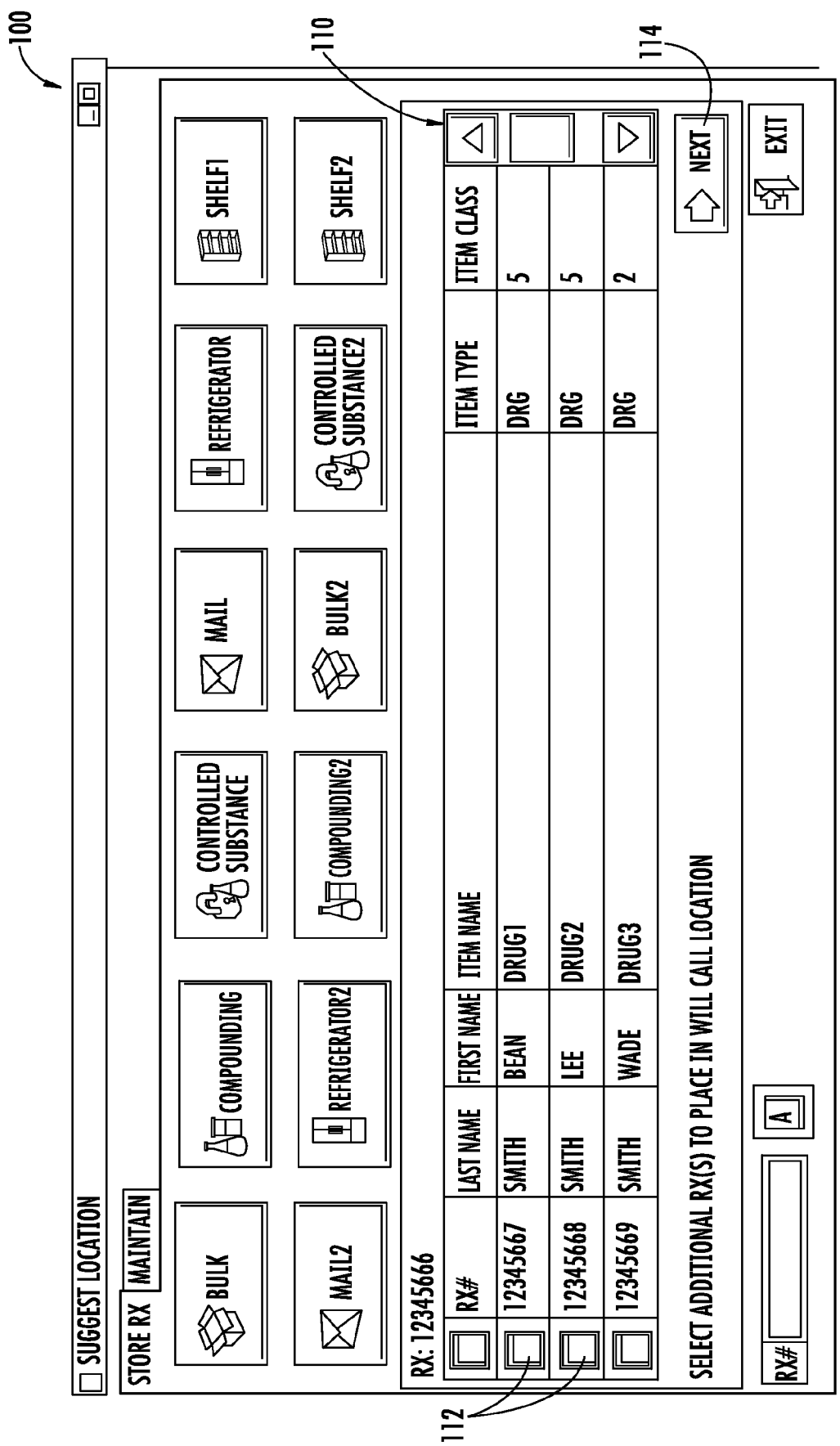
FIG. 15 shows an example of another Store screen of a Virtual Will Call module according to an exemplary embodiment of the present invention.
Figure 16:
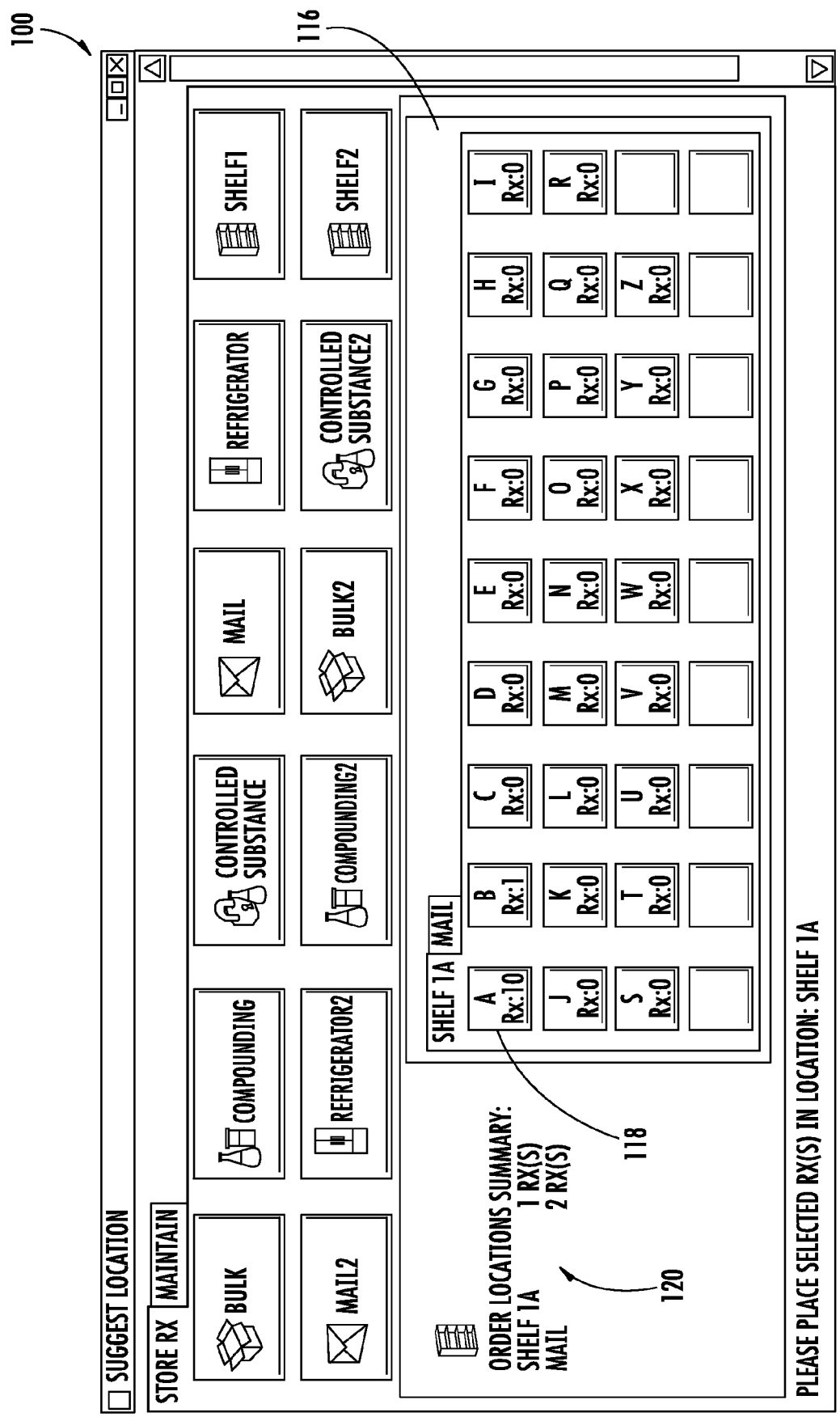
FIG. 16 shows an example of another Store screen of a Virtual Will Call module according to an exemplary embodiment of the present invention.

Any prescriptions belonging to the same order as the entered prescription number may be retrieved from the system and provided in a window 110, shown in FIG. 15, with the entered prescription number listed at the top. Information regarding each prescription number retrieved may also be listed, including the first and last name of the patient, the name of the item, the type of item, and the item class, among others. A check box 112 may also be provided for each entry to allow the user to select the prescriptions to be placed in a particular Will Call location. Upon clicking on the Next button 114, another window 116 may be displayed, as illustrated in FIG. 16. If there are no other items in the same order as the entered prescription number, the window 110 of FIG. 15 is not displayed, and instead the window 116 of FIG. 16 is directly displayed to the user.

In addition to showing the layout of the Storage Area, the window 116 of FIG. 16 may also show the number of prescriptions already stored in each cell of a particular Storage Area. The selected prescriptions may be stored in any available Storage Area in a cell as specified by the user. For example, the user may store the prescription in Shelf 1A, cell A, by clicking on or otherwise selecting the button 118 representing the particular cell. Furthermore, a summary 120 of the will call locations of the prescriptions included in the same order as the entered prescription may be provided, including the location and the number of prescriptions stored in each location.

In some cases, the system may suggest a storage location to the user. For example, the entered prescription number may be for the same item that is currently stored in a certain Storage Area. In that case, the same Storage Area may be suggested to the user for storage of the entered prescription number. In other cases, a Storage Area corresponding to the first letter of the last name of the patient may be suggested.

However, the user may still have the option of ignoring the suggestion and storing the entered prescription number in a location of the user's choosing. In some embodiments, the user may have to authenticate the location selected by scanning the user's identification barcode, scanning the user's finger print, or entering some other type of user identification password or barcode number (e.g., if transactional security is activated).

Figure 17:
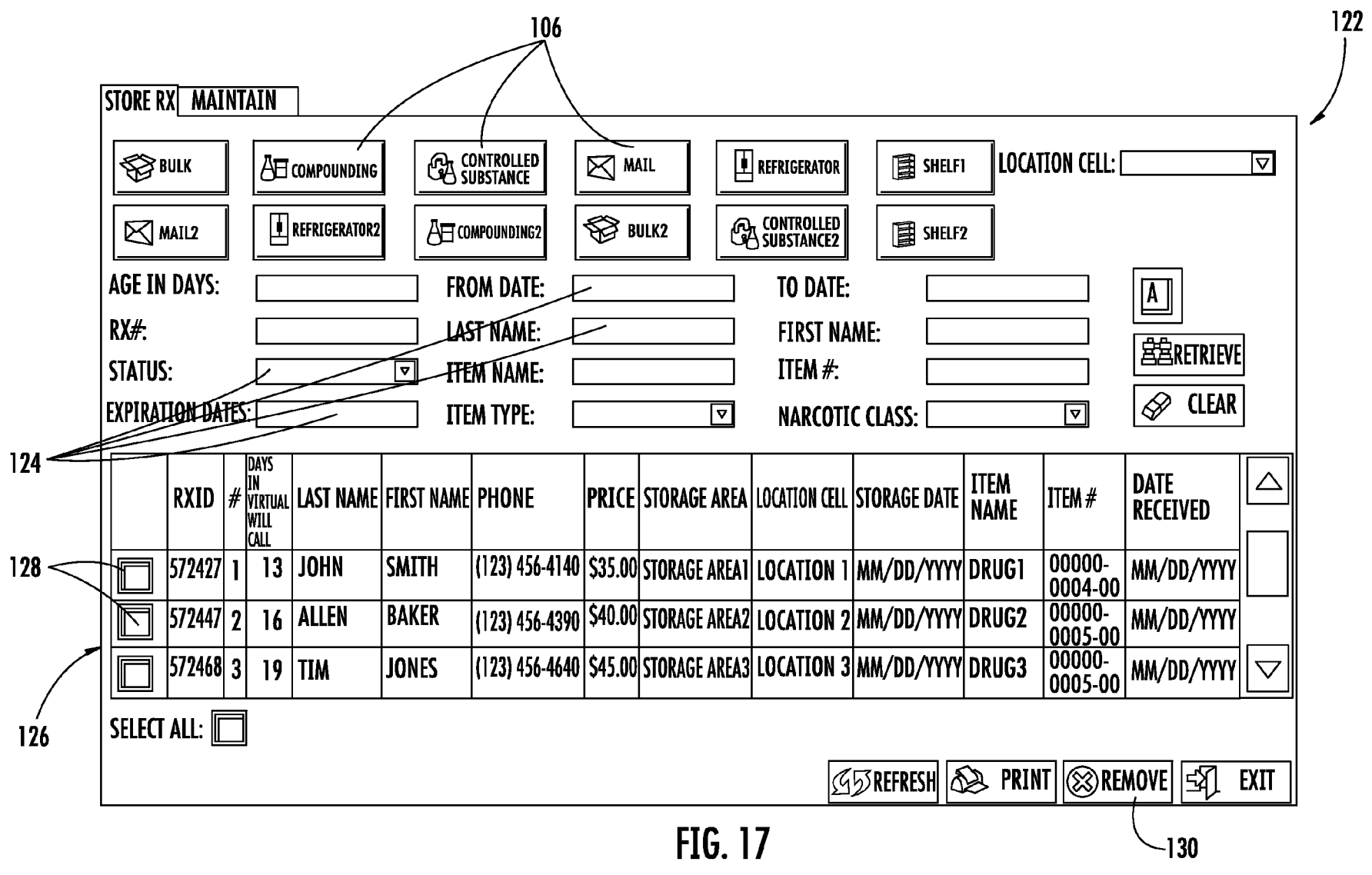

Referring again to FIG. 14, the user may have the ability to maintain the prescriptions already stored in Virtual Will Call by selecting the Maintain tab 104. Selecting the Maintain tab 104 may display a window 122 as illustrated in FIG. 17. The window 122 may include buttons 106 representing each Storage Area as well as several fields 124 to allow a user to enter various search criteria for retrieving a certain prescription record. The search criteria may include the Will Call Storage Area, the Storage Location, the Age in days of the prescription (including Maximum Retention Days and Warning Retention Days), From and To dates, Prescription Number, Dispensing Number, Patient Name, Delivery Method, Item Name, Item Number, Item Class, Item Type, Item Expiration Date, among others. For example, the user may select one of the buttons 106 corresponding to a Storage Area to search the corresponding Storage Area for a particular prescription, or the user may specify the search criteria by entering information in the fields 124.

Results based on the search may be displayed in a table 126, allowing the user to select a checkbox 128 corresponding to the entry of interest. In this way, prescriptions may be removed (for example, when the item has been dispensed to the patient) and information regarding a prescription may be modified or updated. Prescriptions may also be removed by entering the prescription number of the item or scanning its barcode to retrieve the corresponding record and then clicking on the Remove button 130.

Rx Tracker Module

The Rx Tracker module may also be included in the software application. Upon execution, the Rx Tracker module may provide a way to allow authorized pharmacy personnel to track the status of an ordered prescription as well as to view details regarding the prescription and/or the patient.

Figure 18:
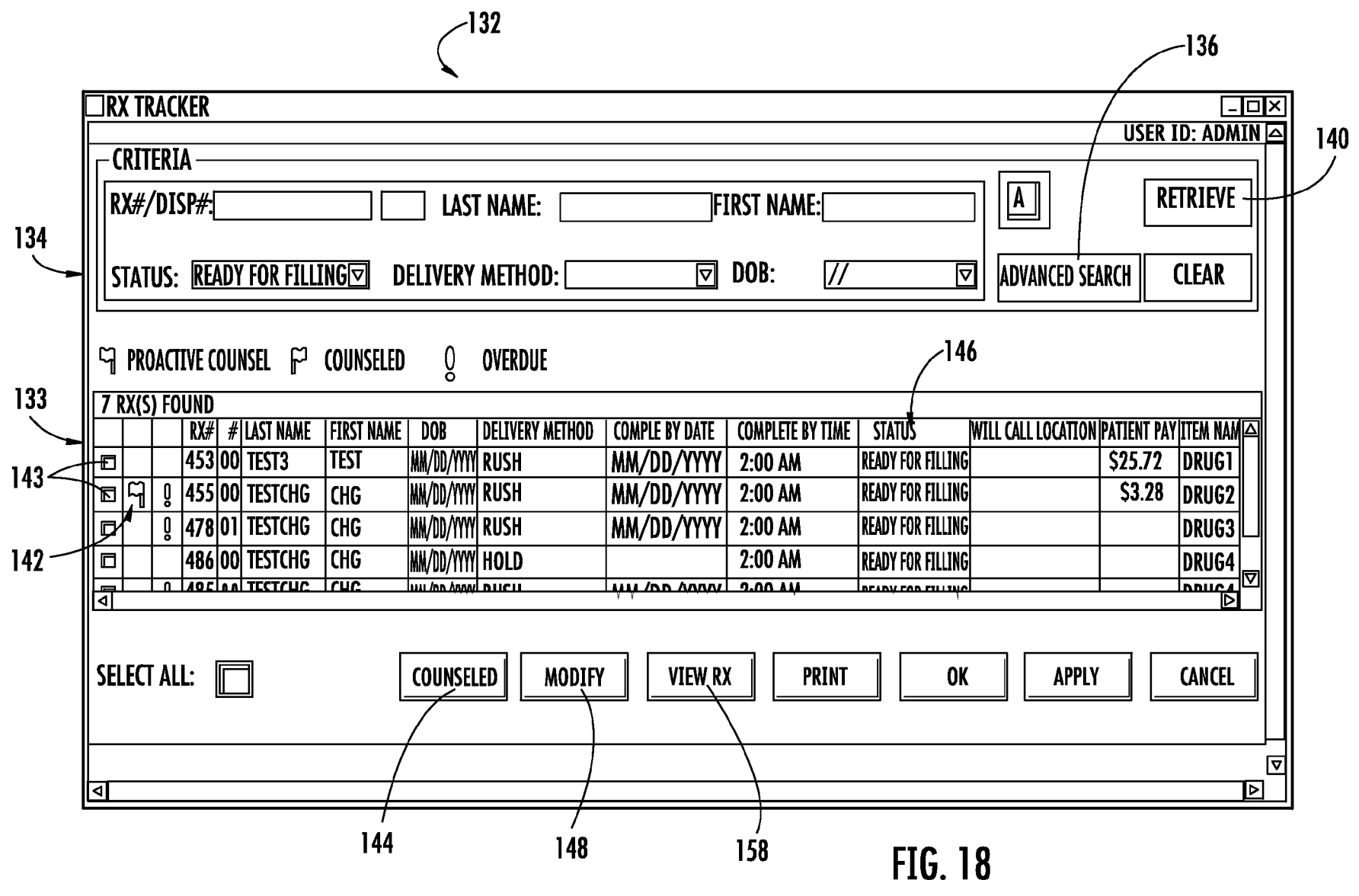

The user may be able to use the Rx Tracker module to search for prescriptions and view prescription details; update the status of a prescription; update the date, time, and delivery method of a prescription; and/or set a particular prescription to "Counseled" (described below). Upon launching the Rx Tracker module, for example by selecting the respective module button 32 from the toolbar 34 (FIG. 2), the Rx Tracker screen 132 may be displayed, as illustrated in FIG. 18. The system may be configured to initially display all the Prescription Dispense records created on that day, for example in a results table 133. The user may specify search criteria 134 by choosing the criteria from among those listed in drop down boxes and/or entering the criteria in text fields. An Advanced Search button 136 may be selected to provide the user with additional search options 138, as shown in FIG. 19.

Figure 19:
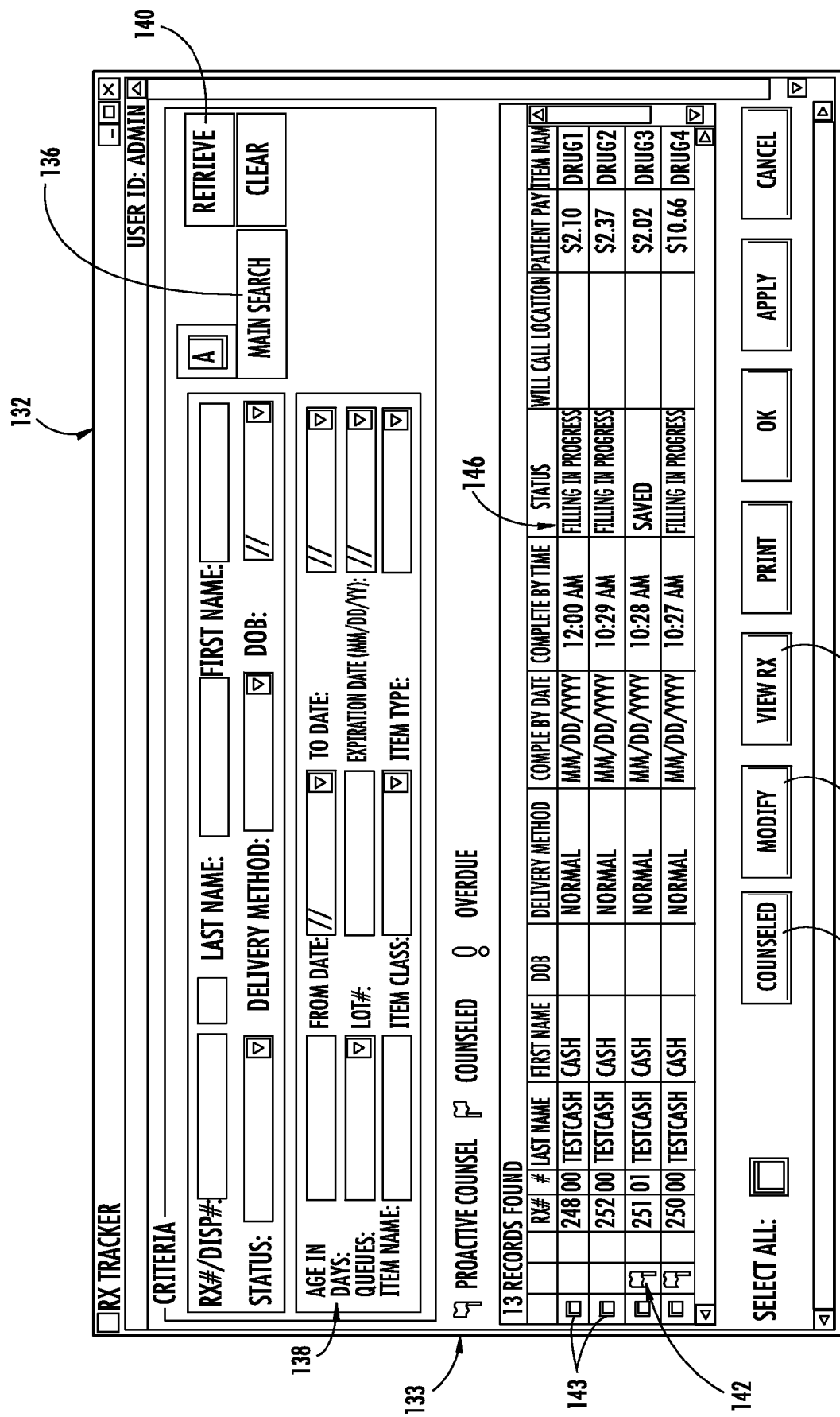
FIG. 19 shows an example of an Advanced Search screen of an Rx Tracker module according to an exemplary embodiment of the present invention.

Referring to FIGS. 18 and 19, once the search criteria have been defined by the user, the user may click on the Retrieve button 140 to initiate the search. Results of the search may then appear in the results table 133, which includes details regarding each record, as shown. For example, each record may include an indication of whether proactive counseling of the patient to whom the item is to be dispensed is required. Proactive counseling may include discussing potential side effects of a prescription with the patient, requesting additional information from the patient, or inquiring about additional symptoms to evaluate the appropriateness of dispensing a particular drug. The indication may be, for example, a red flag 142 by each record for which proactive counseling is required. The inclusion of the red flag 142 may, for example, cause personnel dispensing the item to the patient to summon a pharmacist to counsel the patient as needed before distributing the item. In this regard, comments or notes entered by the pharmacist or other personnel (e.g., at the time the prescription was filled) may be associated with the flag such that the pharmacist may remember the issue to be discussed when the patient comes back to pick up the item. Once the patient has been counseled, the pharmacist may include that fact in the record by changing the indication from "Proactive counseling needed" to "Counseled." This may be done, for example, by selecting the checkbox 143 associated with the particular entry and clicking on the "Counseled" button 144, which may serve to change the indication (e.g., the flag) accordingly.

Figure 20:
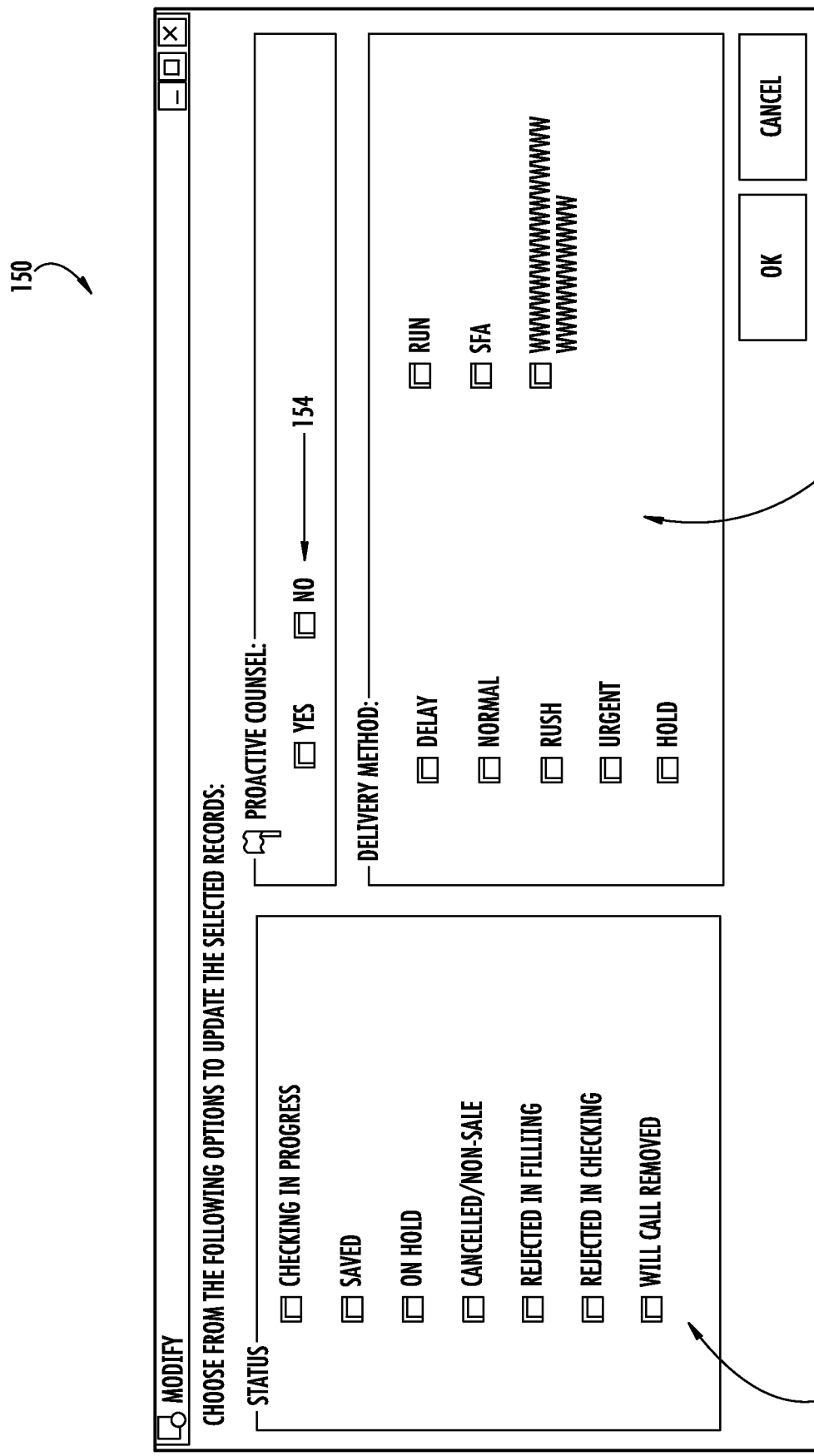
FIG. 20 shows an example of a Modify screen of an Rx Tracker module according to an exemplary embodiment of the present invention.

The status of a given prescription may be displayed as part of the results table 133, such as in a column labeled Status 146. The status of a prescription may include, for example, "Ready for filling," "Filling in progress," or "Saved." Information regarding a particular entry, such as the Status 146, may be modified when an authorized user chooses an entry via the checkbox 143 and clicks on the Modify button 148. Selecting the Modify option may serve to display a Modify screen 150, shown in FIG. 20, which allows the user to make changes such as selecting the appropriate status via a status checkbox 152, activating or deactivating the Proactive Counseling indication 154, and specifying the Delivery Method 156.

Figure 21:
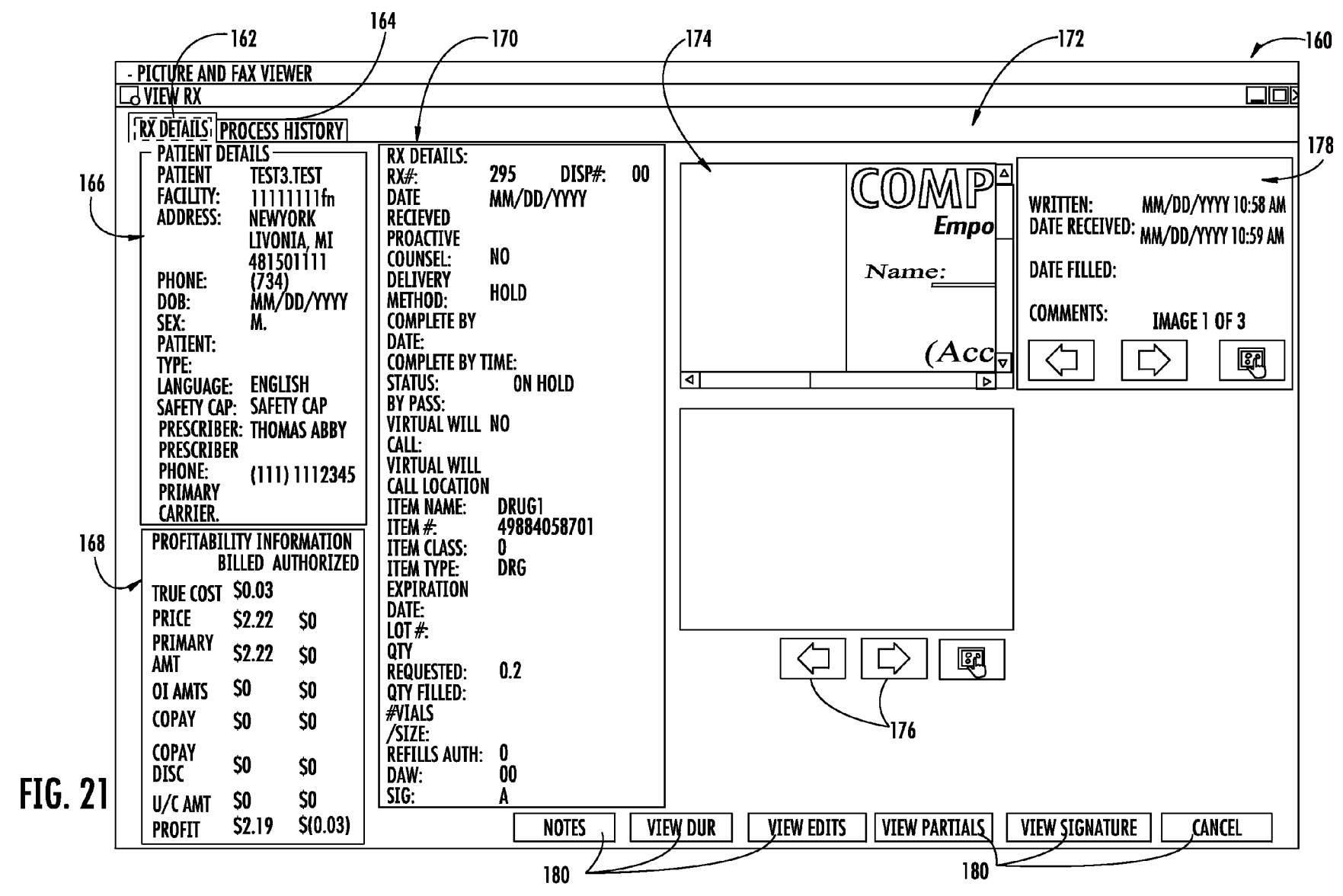

Referring again to FIGS. 18 and 19, details regarding a particular entry or multiple entries may be viewed by a user upon clicking on the View Rx button 158. Selecting the View Rx option may cause a View Rx screen 160 to be displayed, as illustrated in FIG. 21. The View Rx screen 160 in turn may include various tabs of information, such as an Rx Details tab 162 and a Process History tab 164. Information displayed under the Rx Details tab 162 is shown in FIG. 21. Such information may include multiple sections of data, such as a Patient Details section 166, a Profitability Information section 168, an Rx Details section 170, and an Imaging section 172.

The Patient Details section 166 may include various items of information regarding a particular patient associated with the selected prescription, including the patient's name, facility, address, phone number, date of birth, and sex, among many others. Profitability Information 168 may include both the billed and authorized amounts for the prescription, such as the true cost, the price to the patient, copay, discounts, profit, and other financial information. The Rx Details section 170 may include information about the prescription itself, including whether the prescription has been tagged for proactive counseling of the patient, the status of the prescription, the Virtual Will Call location, etc. The Imaging section 172 may include a window 174 for displaying any images associated with the prescription (such as the prescription itself, the patient's driver's license, and the patient's insurance card, among others). The Imaging section 172 may further include a mechanism, such as scrolling arrows 176, to navigate from one image to the next when multiple images are involved, as well as a log 178 summarizing when a particular image was associated with the record and by whom.

Figure 22:
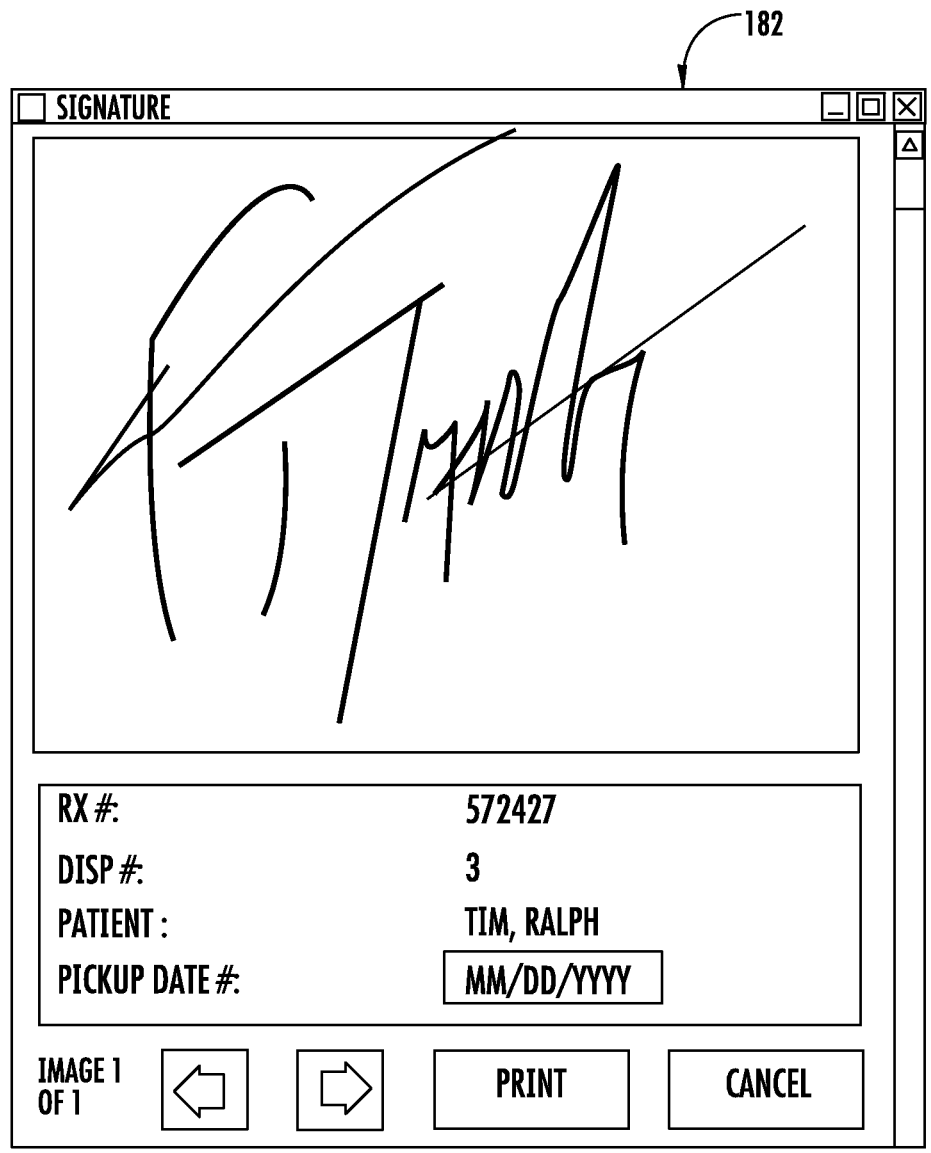
FIG. 22 shows an example of a Signature window of an Rx Tracker module according to an exemplary embodiment of the present invention.

Furthermore, buttons 180 may be included to allow the user to enter notes into the given record, view DUR (Drug Utilization Review) (i.e., any drug conflicts that are listed for the particular prescription), view edits, view partials (i.e., partially filled prescriptions), and view signatures, among other functions. For example, selecting the "View Signature" function may allow the user to view the signature of the patient for various pick up dates of the prescription and may cause a window 182 with an image of the signature and signature details to be displayed, as shown in FIG. 22.

Referring again to FIG. 21, the user may choose to select the Process History tab 164 to view the process history of the particular prescription. Upon selecting the Process History tab 164, the Process History screen 184 depicted in FIG. 23 may be displayed. This screen 184 may list all the activities that have been logged for the prescription since the creation of the record. Such information may include, for example, the date of the activity, the module used, the user responsible for the activity, and a description of the activity, among other information.

System Preferences

The software application may provide the user with the ability to configure the application in various ways. For example, a user with appropriate authorization may be able to set up and customize a delivery method for a particular prescription. Referring to FIG. 24, a user may select a Delivery Method tab 186 from a Preferences section 188 of the software application in order to input customized delivery methods based on the needs of the patients served by the pharmacy. Customized information may be entered in a Delivery Methods table 190 by a user and may include a Delivery Code, a Delivery Method (such as "Delay," "Normal," "Rush," "Urgent," and "Hold"), a Time Type (e.g., minutes, hours, etc.), and a Time Value (i.e., how much time is required for the particular delivery method). Furthermore, one of the delivery methods (such as "Normal") may be designated as a Default delivery method, and unused rows of the table 190 may be designated "Inactive."

A user may either modify an existing delivery method (for example by changing the required time) or may create a new delivery method by undesignating an empty row as Inactive (for adding a new method) and entering the desired information to configure the delivery method. Once a user has entered the desired information in the Delivery Methods table 190, the user may apply the changes by clicking on the Apply button 192. The system may verify that the new or changed delivery method does not duplicate any previously existing delivery methods before allowing the change.

Thus, a delivery method for a prescription may be designated by the user. The delivery method may then be associated with a delivery time of the prescription. As an example, a prescription that is designated as a "Rush" delivery method may be associated with a delivery time of "20 minutes." A list of the prescriptions may then be prioritized according to the delivery method and the associated delivery time for each prescription. In this way, a prescription that is entered earlier in the day but for which the designated delivery method is associated with a longer delivery time may be prioritized lower than a prescription that is entered later in the day but has a delivery method associated with a much shorter delivery time (for example, an "Urgent" delivery method).

In some cases, the delivery method may be associated with a delivery time that is a specific time of day for delivering the prescription, such as 3:00 PM. This delivery time may be entered by the user (for example, based on a customer request), or the delivery time may be estimated based on the time the prescription is entered and the designated delivery method. Furthermore, the system may have a cut-off time, representing a time after which prescriptions will not be filled (i.e., the prescription must wait until the following day to be filled). The cut-off time may be, for example, an hour before the pharmacy is scheduled to close, or the time the pharmacist goes home for the day. In this case, a new prescription that is received after the cut-off time would be set for filling on the following work day. Furthermore, if a prescription is associated with a delivery time that is earlier than the current system date/time (i.e., the delivery time has already passed), the prescription would be set for filling on the following work day. Thus, in an exemplary embodiment, the prescription in these cases would be placed on the Filling Queue for the next work day and thus may appear on the "deferred queue" (see the discussion in the Dashboard Module section).

Other aspects of the application may also be configurable by the user according to the user's preferences. For example, referring to FIG. 30, a packing box configuration may be set by the user according to the needs of the pharmacy. The packing box refers to a location in the pharmacy where prescriptions may be stored between filling and checking operations. Thus, after an order is filled, the order may be placed in a cell of the packing box such that another user may be able to find the order to check that the order was properly filled. In many cases, the packing box is an arrangement of "cubby holes" located between the filling station and the checking station in the pharmacy, such as a grid of cells that is four columns wide and four rows tall (for example). Depending on the configuration of the pharmacy (e.g., different floor plans or the special needs of staff members), some of the cells may be inaccessible or unused during typical pharmacy operations. For example, the person who typically checks the orders may not be able to reach the topmost row of cells; therefore, the person filling prescriptions may choose not to use the topmost row of cells for storing orders for checking.

Figure 30:
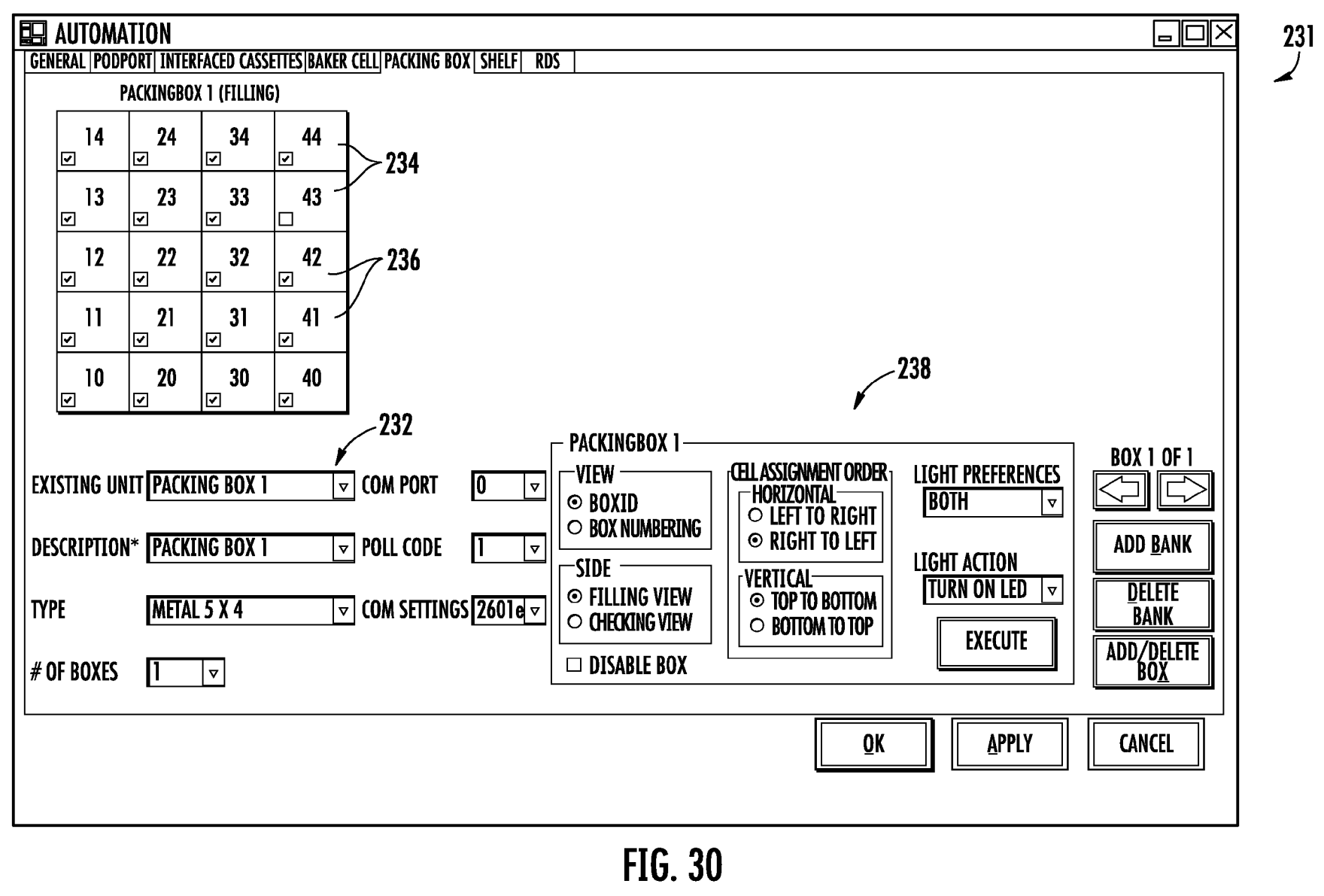

In this regard, the packing box may be represented as a virtual packing box upon execution of the software application to assign and keep track of the cells to be used for the orders. As shown in FIG. 30, an Automation module may include a Packing Box tab 231 that is displayed to a user who is configuring the packing box. Multiple packing boxes may be configured using a drop down menu 232 to select the desired packing box. The corresponding packing box cells 234 may be displayed as they appear to the user who is doing the filling ("Filling View," as shown in the figure) or the user who is doing the checking ("Checking View"), according to the user's preference. Each cell 234 may be associated with a number or other identifying label that corresponds to the packing box in the pharmacy, which is also configurable by the user. Each cell 234 may have a check box 236 that allows the user to select or de-select the packing box cells 234 that will be used. For example, if cell number 43 is obstructed based on the pharmacy configuration and is therefore unusable, the corresponding check box 236 for cell number 43 may be de-selected to indicate that this particular cell should not be used for cell assignment. In this way, the de-selected cells would be skipped during cell assignment and the next available cell in the assignment order would be used.

In the event that a prescription resides in a cell that has been de-selected for future use, that cell may continue to be used until the prescription is finished. Once the prescription is completed and is no longer in the cell, no further assignments would be made to that cell. Furthermore, a de-selected cell may appear in the Checking View as an empty cell.

The order in which selected cells are assigned may also be configurable by the user via a Cell Assignment Order section 238 of the screen. Radio buttons may be selected or de-selected to indicate the horizontal order of assignment (left to right or right to left) as well as the vertical order of assignment (top to bottom or bottom to top). The assignment order shown in FIG. 30, for example, is right to left and top to bottom. Thus, in this case, cell 44 would be the first cell assigned and cell 10 would be the last cell assigned in the packing box shown. In this example, because cell 43 is de-selected, assignment of cell 14 would be followed by assignment of cell 33, then cell 23, etc.

Archive Viewer Module

The Archive Viewer module may be included in the software application to allow the user to store a record of certain important images associated with a prescription in a location of the user's choice. For example, certain laws and regulations, such as the Health Information Privacy Accountability Act (HIPAA) may require that some documents involved in the filling and dispensing of a prescription (e.g., the prescription itself and releases signed by the patient) be maintained by the pharmacy for a number of years after the prescription has been dispensed. Rather than using valuable space in the pharmacy to physically store hardcopies of such documents, an image of the actual document may be stored on a drive or in a memory in such a way that the storage does not negatively affect regular processing operations of the system and such that the image may be easily retrieved for subsequent viewing.

In this regard, the Archive Viewer module may be used to archive images based on selection criteria and create an Archive Viewer executable file, the execution of which will allow a user to view the archived images on any computer (not necessarily the computer via which the image was originally archived). In this way, the Archive Viewer may allow an authorized user to create and maintain a mobile archive of images.

Figure 25:
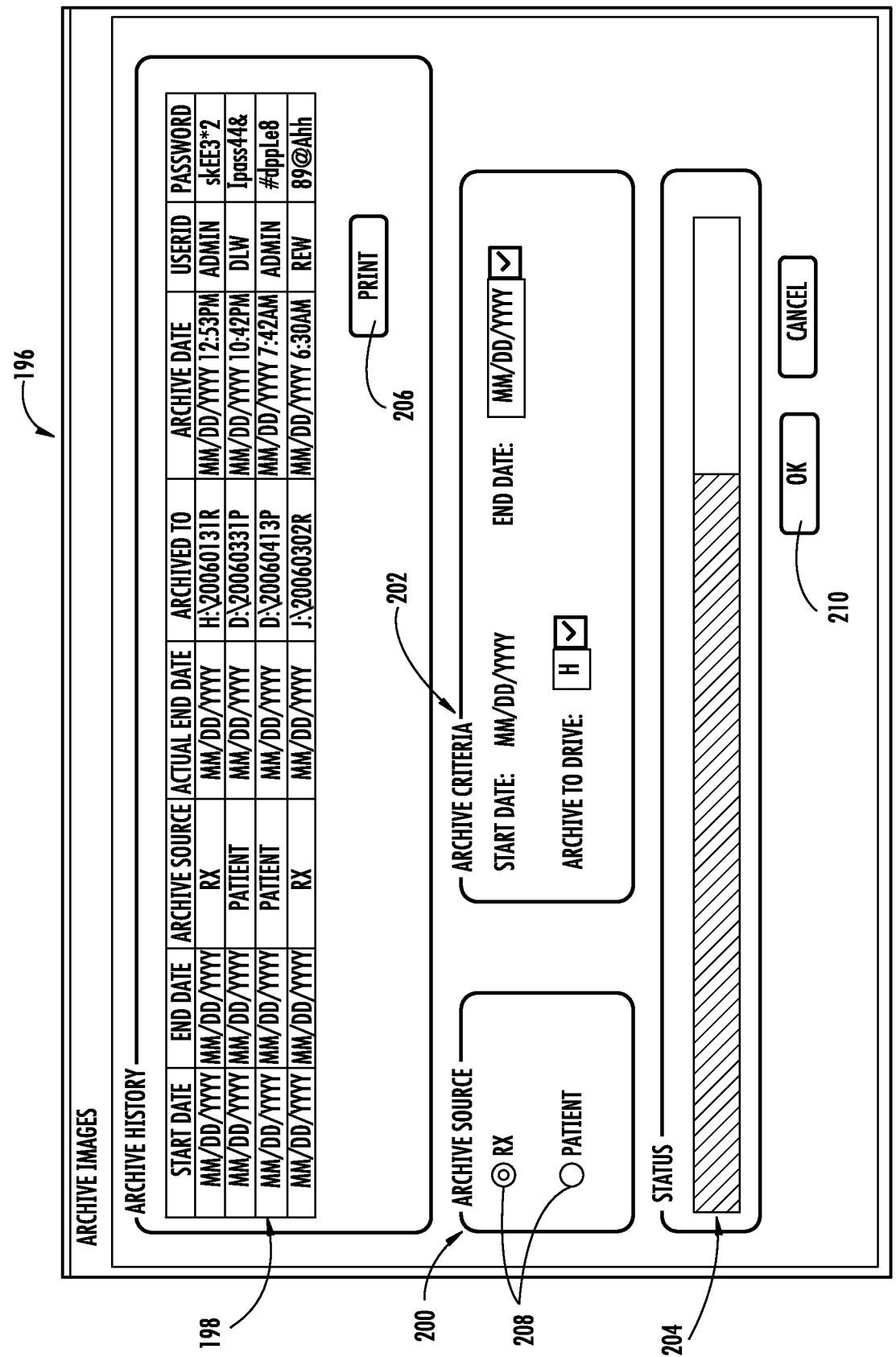
FIG. 25 shows an example of an Archive Images screen of an Archive Viewer module according to an exemplary embodiment of the present invention.

Upon initiating the Archive Viewer, the system may verify that the module is not currently accessed by another user. If the Archive Viewer module is available, an Archive Images screen 196 may be displayed, as shown in FIG. 25. The Archive Images screen 196 may include an Archive History section 198, an Archive Source section 200, an Archive Criteria section 202, and a Status bar 204. The Archive History section 198 may include information regarding past archiving activities, such as the Start Date and End Date of data that was archived, the Archive Source, the Actual End Date of the data that was archived, the location where the data was stored upon archival, the date of the archive activity, the User ID of the user who performed the archive activity, and the password assigned by the user to the archived material. The user may choose to print the Archive History by clicking on the Print button 206.

The user can perform an archive activity by specifying certain information in the Archive Source 200 and Archive Criteria 202 sections of the Archive Images screen 196. The user may select a radio button 208 corresponding to the database from which the images to be archived should be obtained. In FIG. 25, radio buttons 208 for a prescription database (Rx) and patient database (Patient) are listed as options. The user may then specify the dates of the records to be archived under the Archive Criteria section 202. In some cases, as shown in FIG. 25, the Start Date may be pre-selected by the system based on the end date of the last archive activity performed on the respective database. The End Date may be entered by the user or selected from a drop down menu, as illustrated. Furthermore, the location at which the images are to be archived may be entered or selected by the user, such as via a drop down box that is populated by the system. The images may be archived, for example, in local memory (such as on the hard drive of the workstation running the module), in shared memory (such as on a shared drive or a common server), or on a portable memory device (such as a USB device). In some embodiments, the archival process may not be compatible with CDs and DVDs, and thus a user attempting to archive to a CD or DVD may be prompted to choose a different target drive. Once the requisite criteria are specified, the user may click on the OK button 210 to initiate the archive activity.

Figure 26:
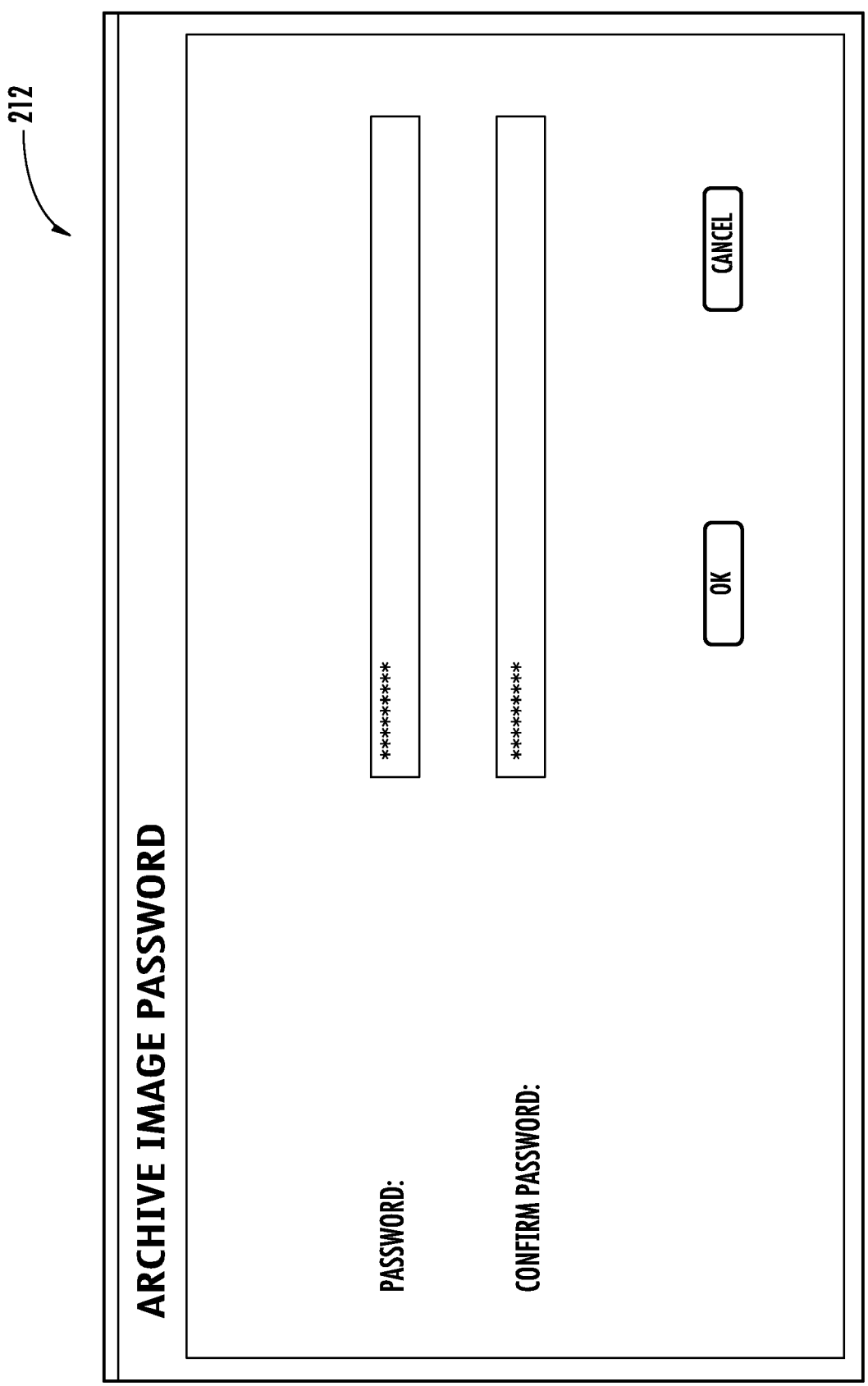
FIG. 26 shows an example of a Password screen of an Archive Viewer module according to an exemplary embodiment of the present invention.

At this point, the system may verify that the criteria specified is valid (e.g., valid drive designation and date ranges) and may prompt the user to enter a password to protect the images about to be archived (e.g., via encryption), for example by displaying a Password screen 212 as shown in FIG. 26. The user may then enter a password and may be required to confirm the password by entering it a second time. Referring again to FIG. 25, the system may then create an archive log within the database specified in the Archive Source 200 to make a record of the archive activity. In some cases, this involves adding an entry to an archive history table on the target drive. The system may also validate that enough space exists in the location specified as the archive destination in the Archive Criteria section 202 and, if the space is not adequate, may prompt the user to specify a different location. If the space is adequate, the archive process may continue, and the records and associated images may be retrieved, encrypted (using the password as the hash key), and archived. A first tag of the dataset may be made including the data and a time stamp of the archival, and a second tab may include the password that was chosen by the user for the encryption. In some embodiments, the encrypted data may be serialized in dataset format to an xml file and stored (along with an archive viewer executable, discussed below) on the target drive. However, this is only one technique, and the data may be archived in other formats and according to other suitable protocols.

Figure 27:
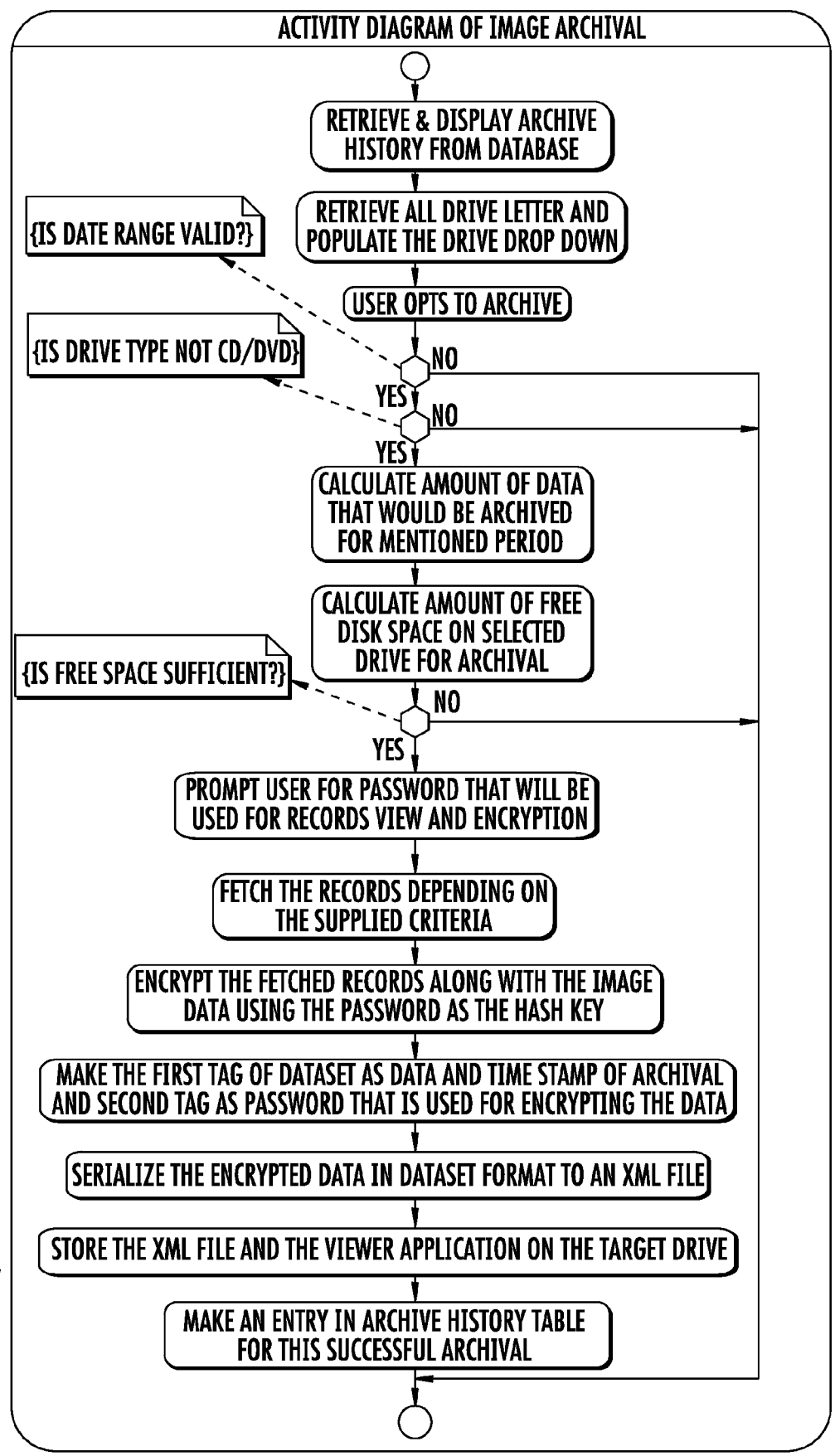
FIG. 27 is a flow chart illustrating the archive process of an Archive Viewer module according to an exemplary embodiment of the present invention.

An archive viewer executable may be created within an archive folder created in the specified destination. Thus the archive viewer executable is normally stored on each drive/memory device on which the archived data is stored. The archive viewer executable may be executed to permit subsequent viewing of the archived data stored on the drive/memory device. In this way, a user may later view the image by invoking the archive viewer executable to initiate an archive viewing interface, independent of the Archive Viewer module. The status of the archival process may be depicted on the screen 196, for example through the use of a Status bar 204. A summary of the steps involved in the archive process is included in FIG. 27.

If the Archive Viewer is being used by someone else (and is therefore locked) when the user attempts to perform an archive activity, the user may be given the option to unlock the archive image process. This may be useful in the case that another user has already performed an archive activity but has forgotten to log off the module. However, if the other user is currently engaged in an archival activity, unlocking the archive image process may cause the module to abandon the archival activity underway in order to unlock the module for use by the new user. In this case the system may log the details of the last successful date archived for the original user (i.e., the point in the archival process at which the activity was interrupted).

Figure 28:
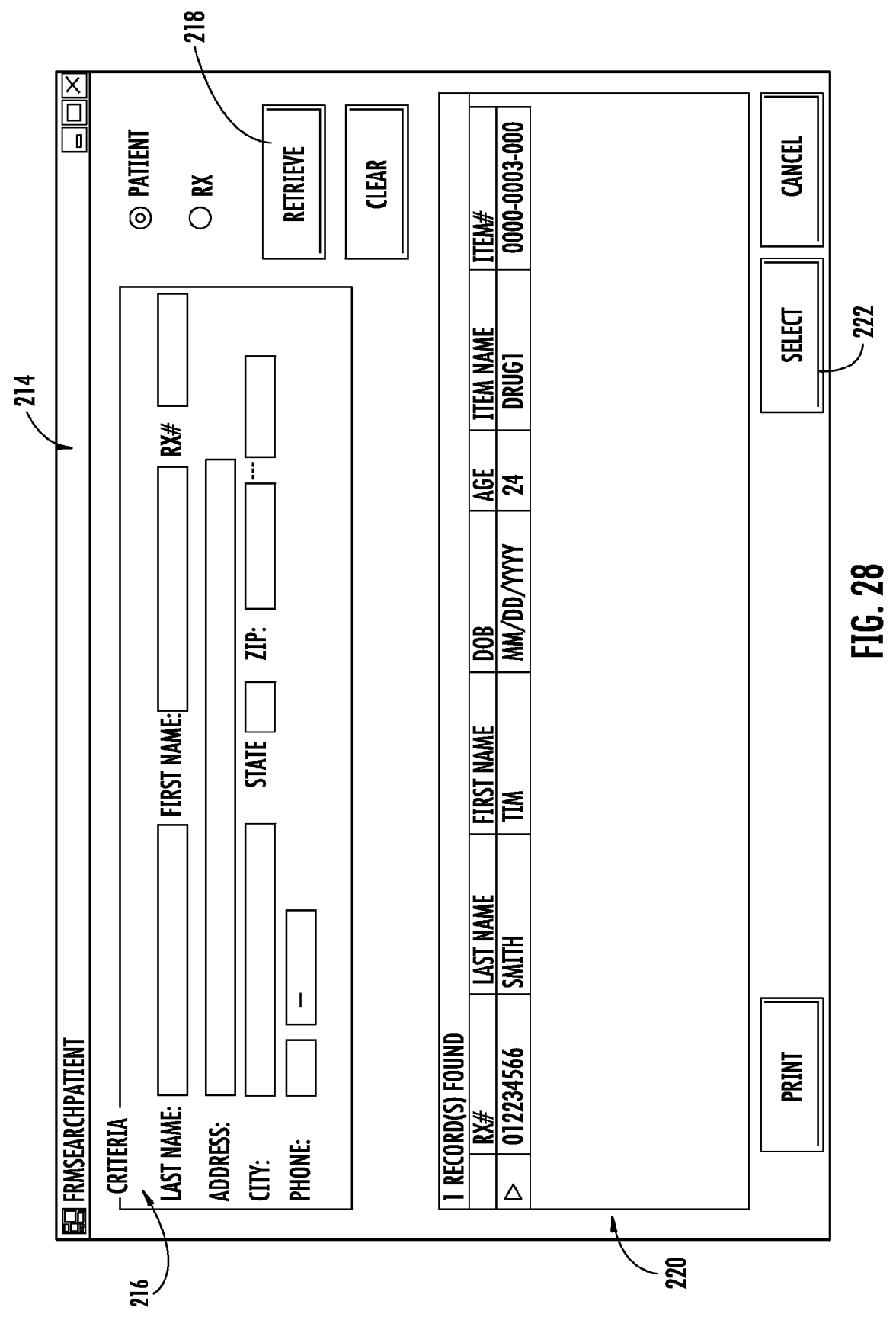
Figure 29:
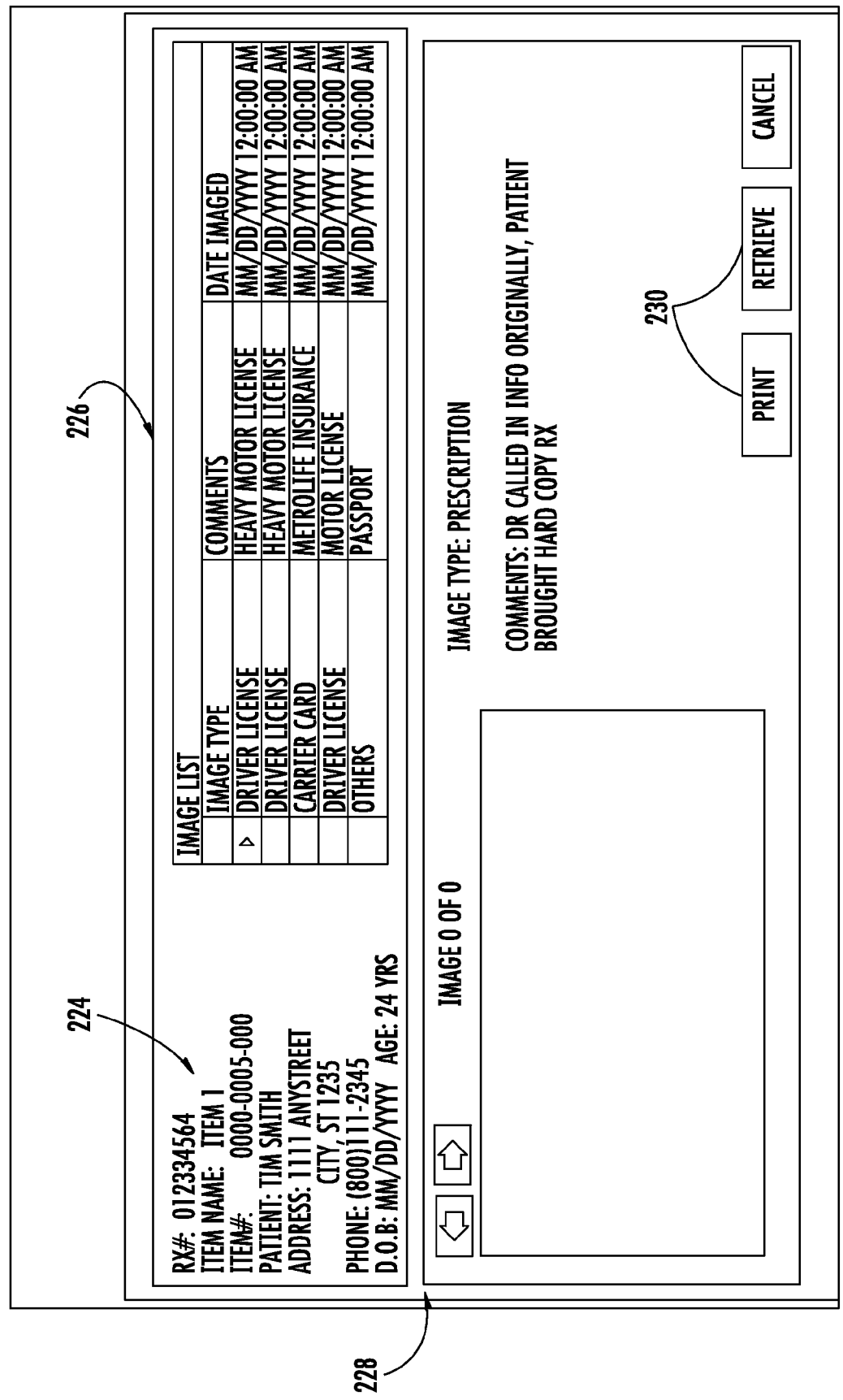
FIG. 29 shows an example of a Selected Record screen of an Archive Viewer module according to an exemplary embodiment of the present invention.

When a user wishes to view an image that has been archived, and the user has access to the drive in which the archive file resides, the user may launch the viewer (independently of the Archive Viewer module) by invoking the archive viewer executable created in the same drive/memory device. The user may then be prompted to enter the password protecting the archived image and, upon verifying the password, may retrieve the archived file. The user may then be prompted via a Search screen 214, illustrated in FIG. 28, to enter search criteria 216 to select the desired archived records for viewing. The search criteria may include the patient's name, prescription number, address, or phone number, among other items of information. Once the search criteria 216 are specified, the user may click on the Retrieve button 218 to retrieve the desired records. Based on the search criteria, the matching records may then be retrieved and displayed to the user in a Results window 220. The user may highlight the desired record and click on the Select button 222 to display a summary of the record 224 and a list of the images 226 associated with the selected record, as shown in FIG. 29.

The user may select one of the images listed in the Image List 226, for example by clicking on the corresponding entry in the list 226, to display the image or a portion of the image in the Image window 228. Additional information, such as the Image Type and any comments associated with the image, may also be displayed in the Image window 228. The selected image may then be printed or retrieved for viewing in full using the appropriate buttons 230.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of managing activities for a medical service provider comprising:
   accessing and displaying a plurality of queues and a count of prescriptions in each queue, wherein each queue represents a step in a process of dispensing medication to a patient;
   determining, via a processor, productivity data including at least one user name and a number of prescriptions handled over a predetermined period of time by each user and displaying the productivity data;
   interfacing with at least one independently operable automation unit and displaying a list of each interfacing automation unit; and
   calculating profitability information including amounts paid for prescriptions and amounts approved for payment and displaying the profitability information.

2. The method of claim 1, wherein displaying the queues comprises providing a histogram including a representation of at least one queue selected from the group consisting of a Pharmacy Management queue, an Imaging queue, a Filling queue, a Checking queue, and a Will Call queue.

3. The method of claim 2, wherein providing the histogram comprises differently depicting different subsections of each queue within each representation.

4. The method of claim 1, wherein displaying the queues comprises providing an indication of at least one event associated with at least one of the queues.

5. The method of claim 4, wherein providing the indication includes permitting a selection of the indication such that the selection provides for a display of additional information regarding the respective indication.

6. The method of claim 1, wherein displaying the productivity data comprises providing a log in status of each user and providing a list of log in and log out times upon selection of a respective user.

7. The method of claim 1, wherein displaying the productivity data comprises providing the productivity data in at least one form selected from the group consisting of a graphical representation and a tabular representation.

8. The method of claim 1, wherein interfacing with the at least one automation unit comprises providing at least one characteristic of each interfaced automation unit selected from the group consisting of a number of cells that need replenishment and a number of cells that need cleaning.

9. The method of claim 1, wherein displaying the profitability information comprises receiving a designation of a time period over which the profitability information is calculated and displayed.

10. The method of claim 1 further comprising displaying a graphical representation of at least one workflow characteristic selected from the group consisting of a prescription volume and an average cycle time for processing prescriptions.

11. A computer program product comprising at least one non-transitory computer-readable storage medium having computer-executable program code portions stored therein, the computer-executable program code portions comprising program code instructions for:
    accessing and displaying a plurality of queues and a count of prescriptions in each queue, wherein each queue represents a step in a process of dispensing medication to a patient;
    determining productivity data including at least one user name and a number of prescriptions handled over a predetermined period of time by each user and displaying the productivity data;
    interfacing with at least one independently operable automation unit and displaying a list of each interfacing automation unit; and
    calculating profitability information including amounts paid for prescriptions and amounts approved for payment and displaying the profitability information.

12. The computer program product of claim 11, wherein the program code portions for displaying the queues further comprise program code portions for providing an indication of at least one event associated with at least one of the queues.

13. The computer program product of claim 12, wherein the program code portions for providing the indication further comprise program code portions for permitting a selection of the indication such that the selection provides for a display of additional information regarding the respective indication.

14. The computer program product of claim 11, wherein the program code instructions for displaying the queues further comprise program code instructions for providing a histogram including a representation of at least one queue and differently depicting different subsections of each queue within each representation.

15. The computer program product of claim 11, wherein the program code instructions for interfacing with the at least one automation unit further comprise program code portions for providing at least one characteristic of each interfaced automation unit selected from the group consisting of a number of cells that need replenishment and a number of cells that need cleaning.

16. A system for managing activities for a medical service provider comprising:
    a user workstation configured to access information, display the information to a user, and receive user input;
    at least one independently operable automation unit; and
    a server in communication with the at least one automation unit and the user workstation, wherein the server is configured to provide information to the user workstation for display in response to the user input received via the user workstation, wherein the user workstation is configured to:
    access and display a plurality of queues and a count of prescriptions in each queue, wherein each queue represents a step in a process of dispensing medication to a patient;
    determine productivity data including at least one user name and a number of prescriptions handled over a predetermined period of time by each user and display the productivity data;
    interface with the at least one independently operable automated unit and display a list of each automation unit in communication with the server; and
    calculate profitability information including amounts paid for prescriptions and amounts approved for payment and display the profitability information.

17. The system of claim 16, wherein the user workstation is configured to display an indication of at least one event associated with at least one of the queues.

18. The system of claim 17, wherein the user workstation is configured to receive a selection of the indication such that the selection provides for a display of additional information regarding the respective indication.

19. The system of claim 16, wherein the user workstation is configured to display a histogram including a representation of at least one queue and to differently depict different subsections of each queue within each representation.

20. The system of claim 16, wherein the user workstation is configured to display at least one characteristic of each automation unit in communication with the server, the at least one characteristic being selected from the group consisting of a number of cells that need replenishment and a number of cells that need cleaning.

\* \* \* \* \*

UNITED STATES PATENT AND TRADEMARK OFFICE
CERTIFICATE OF CORRECTION

PATENT NO.       : 8,589,181 B2                                        Page 1 of 1
APPLICATION NO.  : 13/434309
DATED            : November 19, 2013
INVENTOR(S)      : Berzansky et al.

It is certified that error appears in the above-identified patent and that said Letters Patent is hereby corrected as shown below:

On the Title page,
Item (75) Inventors: "Kristi Innocenti Berzansky" should read --Kristie Innocenti Berzansky--.

Signed and Sealed this
Fourth Day of August, 2015

Michelle K. Lee
*Director of the United States Patent and Trademark Office*